(12) United States Patent
Zhang et al.

(10) Patent No.: US 11,083,690 B2
(45) Date of Patent: *Aug. 10, 2021

(54) ENTERIC ELASTOMERS

(71) Applicants: Massachusetts Institute of Technology, Cambridge, MA (US); The Brigham and Women's Hospital, Inc., Boston, MA (US); Tokitae LLC, Bellevue, WA (US)

(72) Inventors: Shiyi Zhang, Shanghai (CN); Andrew Bellinger, Wellesley, MA (US); Carlo Giovanni Traverso, Newton, MA (US); Robert S. Langer, Newton, MA (US); Dean Liang Glettig, Cambridge, MA (US); Lowell L. Wood, Jr., Bellevue, WA (US); Philip A. Eckhoff, Kirkland, WA (US)

(73) Assignees: Massachusetts Institute of Technology, Cambridge, MA (US); The Brigham and Women's Hospital, Inc., Boston, MA (US); Tokitae LLC, Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/528,197

(22) Filed: Jul. 31, 2019

(65) Prior Publication Data
US 2020/0030234 A1 Jan. 30, 2020

Related U.S. Application Data

(63) Continuation of application No. 15/317,601, filed as application No. PCT/US2015/035425 on Jun. 11, 2015, now Pat. No. 10,413,507.

(Continued)

(51) Int. Cl.
A61K 9/00 (2006.01)
C08G 18/73 (2006.01)
(Continued)

(52) U.S. Cl.
CPC .......... *A61K 9/0065* (2013.01); *A61K 9/0053* (2013.01); *A61K 9/48* (2013.01);
(Continued)

(58) Field of Classification Search
None
See application file for complete search history.

(56) References Cited

U.S. PATENT DOCUMENTS 10,413,507 B2 * 9/2019 Zhang .................. A61K 9/0065
2006/0182788 A1 * 8/2006 Singh ..................... A61L 15/44
424/448

OTHER PUBLICATIONS

Zu, Y., et al., Effect of Neutralization of Poly(Methacrylic Acid-co-ethyl Acrylate) on Drug Release From Enteric-coated Pellets Upon Accelerated Storage, Drug Dev. Ind. Pharm., 4 (2007) pp. 457-473. (Year: 2007).*

(Continued)

*Primary Examiner* — Dominic Lazaro
(74) *Attorney, Agent, or Firm* — Wolf, Greenfield & Sacks, P.C.

(57) ABSTRACT

Enteric elastomers and related methods are generally provided. In some embodiments, the enteric elastomer is a polymer composite. Certain embodiments comprise a polymer composite in which hydrogen bonds within two carboxyl group-containing polymers cross-link the polymer networks into an elastic and pH-responsive polymer composite. Advantageously, this polymer composite has the capacity of being stable and elastic in an acidic environment such as that of the stomach but can be dissolved in a neutral pH environment such as that of the small and large intestines. In some embodiments, the polymer composites (Continued)

described herein comprise a mixture of two or more polymers with carboxyl functionality such that the two or more polymers form hydrogen bonds. In certain embodiments, the polymer composite has both enteric and elastic properties.

28 Claims, 25 Drawing Sheets

Related U.S. Application Data

(60) Provisional application No. 62/010,992, filed on Jun. 11, 2014.

(51) Int. Cl.

| | |
|---|---|
| C08G 63/08 | (2006.01) |
| C08G 18/42 | (2006.01) |
| A61K 47/58 | (2017.01) |
| A61K 47/69 | (2017.01) |
| A61K 9/48 | (2006.01) |
| A61K 31/357 | (2006.01) |
| A61K 31/65 | (2006.01) |
| A61K 31/7048 | (2006.01) |
| C08G 83/00 | (2006.01) |
| A61K 47/32 | (2006.01) |
| C08L 33/02 | (2006.01) |
| C08L 33/08 | (2006.01) |
| C08L 33/14 | (2006.01) |
| A61K 47/10 | (2017.01) |
| A61K 47/34 | (2017.01) |
| A61K 47/40 | (2006.01) |
| A61K 47/42 | (2017.01) |
| A61M 31/00 | (2006.01) |

(52) U.S. Cl.
CPC ............ *A61K 31/357* (2013.01); *A61K 31/65* (2013.01); *A61K 31/7048* (2013.01); *A61K 47/10* (2013.01); *A61K 47/32* (2013.01); *A61K 47/34* (2013.01); *A61K 47/40* (2013.01); *A61K 47/42* (2013.01); *A61K 47/58* (2017.08); *A61K 47/6901* (2017.08); *A61M 31/002* (2013.01); *C08G 18/4277* (2013.01); *C08G 18/73* (2013.01); *C08G 63/08* (2013.01); *C08G 83/006* (2013.01); *C08L 33/02* (2013.01); *C08L 33/08* (2013.01); *C08L 33/14* (2013.01); *C08G 2230/00* (2013.01); *C08L 2203/02* (2013.01); *Y02A 50/30* (2018.01)

(56) References Cited

OTHER PUBLICATIONS

Kao (Kao, E.C., et al., Preparation of glass ionomer cement using N-acryloyl-substituted amino acid monomer—Evaluation of physical properties, Dent. Mater. 12 (1996) pp. 44-51). (Year: 1996).*

* cited by examiner

Synthesis of A6ACA

Synthesis of PA6ACA

Synthesis of A11AUA

Synthesis of P(A6ACA$_{0.5}$-CO-A11AUA$_{0.5}$)

ENTERIC ELASTOMERS

RELATED APPLICATIONS

This application is a Continuation of U.S. application Ser. No. 15/317,601, filed on Dec. 9, 2016, entitled "ENTERIC ELASTOMERS," which is a national stage application under 35 U.S.C. § 371 of International Patent Application Serial No. PCT/US2015/035425, filed on Jun. 11, 2015, entitled "ENTERIC ELASTOMERS," which claims priority under 35 U.S.C. § 119(e) to U.S. Provisional Application Ser. No. 62/010,992, filed Jun. 11, 2014, the contents of which are incorporated herein by reference in their entirety for all purposes.

STATEMENT OF GOVERNMENT SUPPORT

This invention was made with Government support under Grant No. R37 EB000244 awarded by the National Institutes of Health (NIH). The Government has certain rights in the invention.

FIELD OF THE INVENTION

Embodiments described herein generally relate to enteric elastomers and related methods.

BACKGROUND OF THE INVENTION

Structures resident in the stomach have been used for a variety of clinical applications including nutritional modulation for bariatrics, ingestible electronics for diagnosis and monitoring, and gastric retentive dosage forms for prolonged drug delivery. Many such structures incorporate elastic polymers to compress large structures during delivery through narrow orifices including the esophagus. However, the non-degradable/non-dissociable nature of these materials risk intestinal obstruction in the setting of accidental structure fracture or migration. These complications have been observed across a range of structures including ingestible electronic structures, percutaneous feeding tubes as well as intragastric balloons for weight loss. Furthermore, previous attempts at gastric residence for drug delivery included mucoadhesion, gastric swelling, and flotation on gastric fluids. However, none of these approaches have demonstrated gastric residence for more than 24 hours, let alone progressed to clinical use.

Despite of the broad and increasing clinical utility of these structures, there is still a need for a mechanism or material which prevents intestinal obstruction upon exiting the stomach.

SUMMARY OF THE INVENTION

Enteric elastomers and related methods are generally provided.

In one aspect, polymer composites are provided. In some embodiments, the polymer composite comprises a first polymer comprising a structure as in Formula (I):

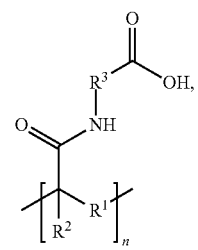

or a pharmaceutically acceptable salt thereof, wherein each $R^1$ is the same or different and is selected from the group consisting of optionally substituted alkylene, optionally substituted heteroalkylene, optionally substituted arylene, and optionally substituted heteroarylene, each $R^2$ is the same or different and is selected from the group consisting of hydrogen, optionally substituted alkyl, and optionally substituted heteroalkyl, each $R^3$ is the same or different and is selected from the group consisting of optionally substituted alkylene and optionally substituted heteroalkylene, n is an integer between 25 and 250,000, and a second polymer comprising a structure as in Formula (II) hydrogen bonded to the first polymer:

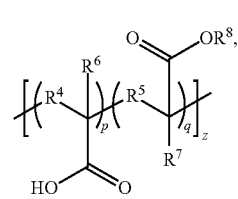
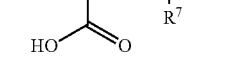

or a pharmaceutically acceptable salt thereof, wherein each $R^4$ is the same or different and is selected from the group consisting of optionally substituted alkylene and optionally substituted heteroalkylene, each $R^5$ is the same or different and is selected from the group consisting of optionally substituted alkylene and optionally substituted heteroalkylene, each $R^6$ is the same or different and is selected from the group consisting of hydrogen, optionally substituted alkyl, and optionally substituted heteroalkyl, each $R^7$ is the same or different and is selected from the group consisting of hydrogen, optionally substituted alkyl, and optionally substituted heteroalkyl, each $R^8$ is the same or different and is optionally substituted alkyl, p is an integer between 1 and 10, q is an integer between 1 and 10, and z is an integer between 1 and 150,000, provided that (p+q)*z is greater than or equal to 20.

In another aspect, enteric polymers are provided. In some embodiments, the enteric polymer exhibits reversible elongation when stretched to at least about 50% of its initial length.

In yet another aspect, methods for forming a polymer composite are provided. In some embodiments, the method comprises mixing a first polymer comprising a structure as in Formula (I) and a second polymer comprising a structure as in Formula (II):

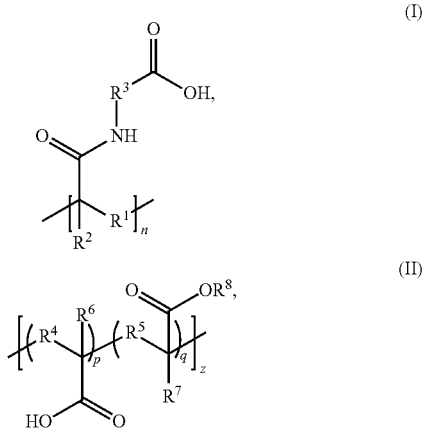

or pharmaceutically acceptable salts thereof, wherein each $R^1$ is the same or different and is selected from the group consisting of optionally substituted alkylene, optionally substituted heteroalkylene, optionally substituted arylene, and optionally substituted heteroarylene, each $R^2$ is the same or different and is selected from the group consisting of hydrogen, optionally substituted alkyl, and optionally substituted heteroalkyl, each $R^3$ is the same or different and is selected from the group consisting of optionally substituted alkylene and optionally substituted heteroalkylene, each $R^4$ is the same or different and is selected from the group consisting of optionally substituted alkylene and optionally substituted heteroalkylene, each $R^5$ is the same or different and is selected from the group consisting of optionally substituted alkylene and optionally substituted heteroalkylene, each $R^6$ is the same or different and is selected from the group consisting of hydrogen, optionally substituted alkyl, and optionally substituted heteroalkyl, each $R^7$ is the same or different and is selected from the group consisting of hydrogen, optionally substituted alkyl, and optionally substituted heteroalkyl, each $R^8$ is the same or different and is optionally substituted alkyl, n is an integer between 25 and 250,000, p is an integer between 1 and 10, q is an integer between 1 and 10, and z is an integer between 1 and 150,000, provided that (p+q)*z is greater than or equal to 20.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
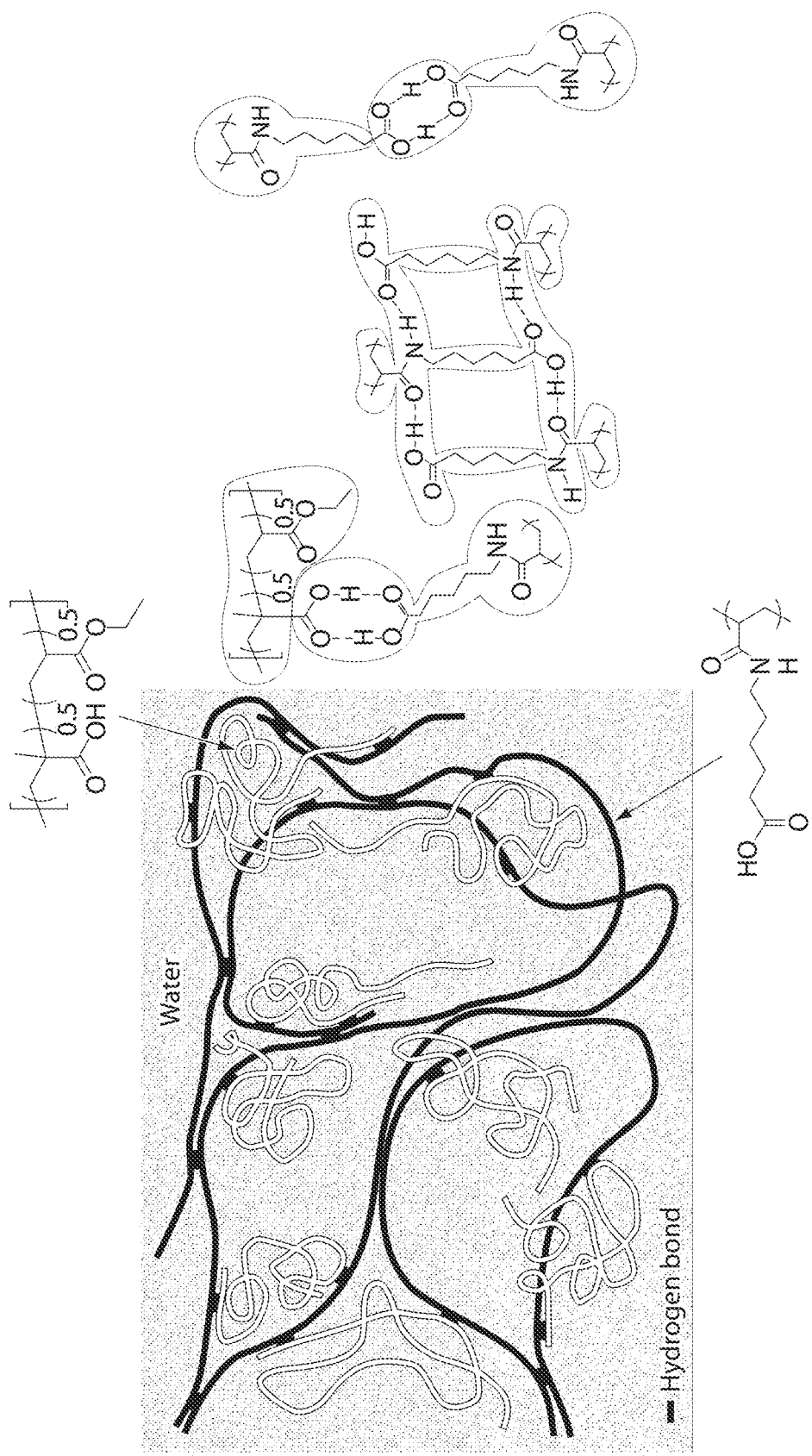
FIG. 1A is a schematic of a polymer composite network, according to one set of embodiments.

Enteric elastomers and related methods are generally provided. In some embodiments, the enteric elastomer is a polymer composite. Certain embodiments comprise a polymer composite in which hydrogen bonds within two carboxyl group-containing polymers cross-link the polymer networks into an elastic and pH-responsive polymer composite. Advantageously, according to certain embodiments, this polymer composite has the capacity of being stable and elastic in an acidic environment such as that of the stomach but can be dissolved in a neutral pH environment such as that of the small and large intestines. In some embodiments, certain of the polymer composites described herein comprise a mixture of two or more polymers with carboxyl functionality such that the two or more polymers form hydrogen bonds. In certain embodiments, the polymer composite has both enteric and elastic properties.

Certain of the polymer composites described herein may be useful in a wide variety of applications including, but not limited to, ingestible electronic structures, drug delivery, biological diagnostics, medical structures, feeding tubes, tissue engineering, veterinary applications, food packaging and environmental engineering applications, as described in more detail below. Enteric polymers are generally known in the art and are typically used as coatings of oral pills and capsules to protect the active pharmaceutical ingredients from the high acidity in the gastric environment. These materials generally share a common structure by having a large hydrophobic moiety and carboxyl groups for pH responsiveness. However, existing enteric polymers are generally rigid and often brittle. Certain of the polymer composites described herein have several advantages over traditional enteric polymers including, for example, the ability to tune the mechanical properties of the polymer composite and the ability to produce polymers with desirable elastic properties and/or flexibility.

The polymer composites described herein are generally elastic. The term elastic generally refers to the ability of a material to substantially return to its original shape spontaneously after contraction, dilatation, or distortion from the original shape. The polymer composites described herein may, according to certain embodiments, offer one or more advantages as compared to traditional enteric polymers, including, but not limited to, mechanical strength sufficient to survive encapsulation and/or mechanical strength sufficient to undergo the compressive forces present in physiological environments such as the gastric environment.

In certain embodiments, the polymer composite may be selected such that it is configured for undergoing large angle deformation for relatively long periods of time without undergoing significant non-elastic deformation. In some such embodiments, the polymer composite may have a strength of recoil sufficient to substantially return polymer composite to its pre-deformed shape within less than about 30 minutes, within less than about 10 minutes, within less than about 5 minutes, or within less than about 1 minute after release of the mechanical deformation. Those skilled in the art would understand that returning to its pre-deformed shape shall be understood to not require absolute conformance to a mathematical definition of shape, but, rather, shall be understood to indicate conformance to the mathematical definition of shape to the extent possible for the subject matter so characterized as would be understood by one skilled in the art most closely related to such subject matter.

In some embodiments, the polymer composite linker has great flexibility. Flexibility can enable packing and/or folding of a structure to, for example, fit into a confined/predefined vessel such as capsule for oral administration or a catheter for endoscopic deployment, as described herein. In some embodiments, the polymer composite has flexibility to 180 degrees to enable tight and/or maximal packing and/or folding.

The polymer composite may be configured for undergoing at least about 45 degrees, at least about 60 degrees, at least about 90 degrees, at least about 120 degrees, at least about 150 degrees, or about 180 degrees of mechanical bending deformation without breaking. In certain embodiments, the polymer composite may be configured for undergoing up to and including about 180 degrees, up to and including about 150 degrees, up to and including about 120 degrees, up to and including about 90 degrees, or up to and including about 60 degrees of mechanical bending deformation without breaking. Any and all closed ranges that have endpoints within any of the above-referenced ranges are also possible (e.g., between about 45 degrees and about 180 degrees, between about 60 degrees and about 180 degrees, between about 60 degrees and about 120 degrees, between about 90 degrees and about 180 degrees). Other ranges are also possible.

In some cases, the polymer composite may be configured for remaining in a deformed configuration (e.g., at least about 45 degrees of mechanical bending deformation) for a relatively prolonged period of time—for example, in some embodiments, the polymer composite has a shelf-life in such a deformed configuration of at least about 24 hours, at least about 1 week, at least about 1 month, at least about 1 year, or at least about 2 years—and still be configured for returning (i.e. recoiling) substantially to its pre-deformation configuration. In certain embodiments, the polymer composite has a shelf life in a deformed configuration of up to and including about 3 years, up to and including about 2 years, up to and including about 1 year, up to and including about 1 month, or up to and including about 1 week and be configured for returning (i.e. recoiling) substantially to its pre-deformation configuration. Any and all closed ranges that have endpoints within any of the above-referenced ranged are also possible (e.g., between about 24 hours and about 3 years, between about 1 week and 1 year, between about 1 year and 3 years). Other ranges are also possible.

Those skilled in the art would be configured for determining suitable methods for tuning the mechanical properties (e.g., elastic modulus, creep behavior) of the polymer composite by, for example, varying the molar ratios of monomeric and/or polymeric units and/or varying the cross-linking density of the polymer.

In certain embodiments, the polymer composite is capable of exhibiting reversible elongation when stretched from 50% to 1500% of its initial length. For example, in some embodiments, the polymer composite is capable of exhibiting reversible elongation when stretched from at least about 50%, at least about 100%, at least about 200%, at least about 400%, at least about 500%, at least about 1000%, at least about 1200%, or at least about 1400% of its initial length. That is to say, in some embodiments, the polymer composite has difference in average length after deformation versus before deformation (e.g., stretching) of less than about 10%, less than about 5%, less than about 2%, or less than about 1%. In certain embodiment, the polymer composite is capable of exhibiting reversible elongation when stretched from less than or equal to about 1500%, less than or equal to about 1400%, less than or equal to about 1200%, less than or equal to about 1000%, less than or equal to about 500%, less than or equal to about 400%, less than or equal to about 200%, or less than or equal to about 100% of its initial length. Any and all closed ranges that have endpoints within any of the above referenced ranges are also possible (e.g., between about 50% and about 1500%, between about hundred percent and about 1500%, between about 200% and about 1000%, between about 500% and about 1400%). Other ranges are also possible.

In certain embodiments, at least one dimension of the polymer composite exhibits reversible elongation when the dimension is deformed from its initial length to a length that is less than about 50% of its original length and/or when the dimension is deformed from its initial length to a length that is at least about 1500% of its initial length. The term reversible elongation, as used herein, generally refers to the ability of a polymer to undergo deformation under tensile stress to a length greater than its initial length, and return substantially to its initial length when the tensile stress is removed. That is to say, in some embodiments, the polymer composite has difference in average length after deformation versus before deformation (e.g., stretching) of less than about 10%, less than about 5%, less than about 2%, or less than about 1%. For example, in some embodiments, the polymer composite exhibits reversible elongation when stretched from at least about 50%, at least about 100%, at least about 200%, at least about 400%, at least about 500%, at least about 1000%, at least about 1200%, or at least about 1400% of its initial length. In certain embodiment, the polymer composite exhibits reversible elongation when stretched from less than or equal to about 1500%, less than or equal to about 1400%, less than or equal to about 1200%, less than or equal to about 1000%, less than or equal to about 500%, less than or equal to about 400%, less than or equal to about 200%, or less than or equal to about 100% of its initial length. Combinations of the above referenced ranges are also possible (e.g., between about 50% and about 1500%, between about hundred percent and about 1500%, between about 200% and about 1000%, between about 500% and about 1400%). Other ranges are also possible.

In certain embodiments, the polymer composite has an elastic modulus ranging between about 0.1 MPa and about 100 MPa. In some embodiments, the elastic modulus of the polymer composite is at least about 0.1 MPa, at least about 0.2 MPa, at least about 0.3 MPa, at least about 0.5 MPa, at least about 1 MPa, at least about 2 MPa, at least about 5 MPa, at least about 10 MPa, at least about 25 MPa, or at least about 50 MPa. In certain embodiments, the elastic modulus of the polymer composite is less than or equal to about 100 MPa, less than or equal to about 50 MPa, less than or equal to about 25 MPa, less than or equal to about 10 MPa, less than or equal to about 5 MPa, less than or equal to about 2 MPa, less than or equal to about 1 MPa, less than or equal to about 0.5 MPa, less than or equal to about 0.3 MPa, or less than or equal to about 0.2 MPa. Combinations of the above referenced ranges are also possible (e.g., between about 0.1 MPa and about 100 MPa, between about 0.3 MPa and about 10 MPa). Other ranges are also possible. Those skilled in the art would be configured for selecting suitable methods for determining the reversible elongation characteristics and/or elastic modulus of an polymer composite including, for example, tensile mechanical characterization under ASTM D638 and/or compressive mechanical characterization under ASTM D575.

In some cases, the polymer composite is not substantially degradable at a first physiological condition (such as in acidic pH such as in the stomach), and is configured for degradation at a second physiological condition different than the first set of physiological conditions, (such as the relatively alkaline pH of the intestines). The term physiological condition generally refers to a set of conditions of the external or internal milleu that may occur in an organism or cellular system (e.g., in contrast to laboratory conditions). For example, in some cases, a physiological condition ranges in temperature between about 20° C. and about 40° C. (e.g., between about 35° C. and about 38° C.) and/or atmospheric pressure of about 1 atm. In certain embodiments, the physiological conditions are that of an internal organ such as the stomach, intestines, bladder, lungs, and/or heart. The polymer composite may be tuned, according to certain embodiments, such that the polymer composite dissolves/degrades after a particular residence time period (e.g., after about 24 hours, after about 48 hours, after about three days, after about seven days, after about one month, after about one year) and/or at a particular range of pH, but is stable at a different range of pH, as described herein.

The polymer composites described herein are, according to certain embodiments, enteric. The term enteric is generally used to describe materials that are stable (e.g., does not substantially dissolve) at relatively highly-acidic pH conditions (e.g., pH of less than about 5.5) and susceptible to dissolution at relatively alkaline pH conditions (e.g., pH of between about 6 and about 9).

In some embodiments, the dissolution of an polymer composite can be triggered by, for example, ingestion of an alkali solution. In some embodiments, the polymer composite has the capacity for dissolution at a pH greater than about 5.5. According to some embodiments, the polymer composite is selected such that the polymer composite is stable in an acidic gastric environment (e.g., having a pH of about 1 to a pH of about 4) but dissolves in a more alkaline region (e.g., having a pH of greater than about 5.5) of the gastrointestinal tract (e.g., such as a portion of the gastrointestinal tract distal to the pylorus).

For example, in certain embodiments, the polymer composite does not substantially dissolve at a pH ranging between about 1 and about 5. In some embodiments, the polymer composite does not substantially dissolve at a pH of at least about 1, at least about 2, at least about 3, at least about 4, or at least about 4.5. In certain embodiments, the polymer composite does not substantially dissolve at a pH of less than or equal to about 5, less than or equal to about 4.5, less than or equal to about 4, less than or equal to about 3, or less than or equal to about 2. Combinations of the above reference ranges are also possible (e.g., between about 1 and about 4.5, between about 1 and about 5, between about 1 and 4). Other ranges are also possible.

In certain embodiments, the polymer composite dissolves substantially at a pH greater than or equal to about 5.5. In some embodiments, the polymer composite dissolves substantially at a pH of at least about 6, at least about 6.5, at least about 7, at least about 7.5, at least about 8, at least about 9, at least about 10, or at least about 11. In certain embodiments, the polymer composite dissolves substantially at a pH of less than or equal to about 12, less than or equal to about 11, less than or equal to about 10, less than or equal to about 9, 8.5, less than or equal to about 8, less than or equal to about 7.5, less than or equal to about 7, less than or equal to about 6.5, or less than or equal to about 6. Combinations of the above reference ranges are also possible (e.g., between about 5.5 and about 12, between about 5.5 and about 9, between about 6.5 and about 8). Other ranges are also possible.

Those skilled in the art would be configured for selecting suitable methods for determining degradation/dissolution of the polymer composites based upon the teachings of the specification including, determining the solubility of the polymer composite in an aqueous solution having a pH of less than about 4 and/or dissolving the polymer composite in aqueous solution having a pH of greater than or equal to about 6, measured at room temperature over time period of between about 2 and about 40 days. In some embodiments, the polymer composite that does not substantially degrade behaves such that less than about 10%, less than about 5%, or less than about 2% of the polymeric composite dissociates from the rest of the polymeric composite. In certain embodiments, the polymer composite that substantially degrades behaves such that at least about 1%, at least about 2%, or at least about 5% of the polymer composite dissociates from the remainder of the polymeric composite.

The polymer composite is, according to certain embodiments, biocompatible. The term "biocompatible," as used herein, refers to a polymer that does not invoke an adverse reaction (e.g., immune response) from an organism (e.g., a mammal), a tissue culture or a collection of cells, or if the adverse reaction does not exceed an acceptable level.

In some embodiments, the polymer composite is cross-linked. In some embodiments, the polymer composite comprises two or more chemically similar polymers or two or more chemically distinct polymers.

In certain embodiments, the polymer composite comprises a mixture of a first polymer and a second polymer. In some embodiments, the first polymer and second polymer are hydrogen bonded. For example, in some cases, a functional group attached to the backbone of a first polymer is hydrogen bonded to a function group attached to the backbone of the second polymer, as described in more detail below.

In some embodiments, the first polymer may comprise Formula (I):

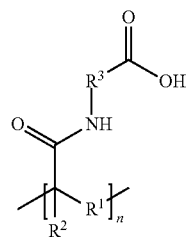

(I)

or a pharmaceutically acceptable salt thereof, wherein:

each $R^1$ is the same or different and is selected from the group consisting of optionally substituted alkylene, optionally substituted heteroalkylene, optionally substituted arylene, and optionally substituted heteroarylene;

each $R^2$ is the same or different and is selected from the group consisting of hydrogen, optionally substituted alkyl, and optionally substituted heteroalkyl;

each $R^3$ is the same or different and is selected from the group consisting of optionally substituted alkylene and optionally substituted heteroalkylene; and n is an integer between 25 and 250,000.

In certain embodiments, each $R^1$ is the same or different and is selected from the group consisting of optionally substituted alkylene and optionally substituted heteroalkylene. In some embodiments, each $R^1$ is the same or different and is selected from the group consisting of optionally substituted $C_{1-10}$ alkylene (e.g., optionally substituted $C_{1-8}$ alkylene, optionally substituted $C_{1-5}$ alkylene, optionally substituted $C_{1-3}$ alkylene) and optionally substituted hetero $C_{1-10}$ alkylene (e.g., hetero $C_{1-5}$ alkylene, hetero $C_{1-3}$ alkylene). In certain embodiments, each $R^1$ is the same or different and is $-[C(R'_2)]_g-$, wherein each R' is the same or different and is selected from the group consisting of hydrogen and optionally substituted alkyl and g is 1, 2, 3, 4, or 5. In some instances, g is 1, 2, or 3 (e.g., g is 1 or 2). In some embodiments, at least one $R^1$ is optionally substituted heteroalkylene, as described herein, and at least one $R^1$ is optionally substituted alkylene, as described herein.

In some embodiments, at least one (e.g., at least two, each) $R^2$ is hydrogen. In some embodiments, at least one $R^2$ is optionally substituted alkyl. In certain embodiments, at least two (e.g., each) $R^2$ are the same or different and are optionally substituted alkyl. In some such embodiments, each $R^2$ is the same or different and is optionally substituted $C_{1-10}$ alkyl (e.g., optionally substituted $C_{1-8}$ alkyl, optionally substituted $C_{1-5}$ alkyl, optionally substituted $C_{1-3}$ alkyl). For example, each $R^2$ may be the same or different and may be methyl or ethyl. In some embodiments, at least one $R^2$ is optionally substituted heteroalkyl. In some embodiments, at least two (e.g., each) $R^2$ are the same or different and are optionally substituted heteroalkyl. In some embodiments, at least one $R^2$ is optionally substituted heteroalkyl, as described herein, and at least one $R^2$ is optionally substituted alkyl, as described herein.

In some embodiments, each $R^3$ is the same or different and is selected from the group consisting of optionally substituted $C_{1-10}$ alkylene (e.g., optionally substituted $C_{2-10}$ alkylene, optionally substituted $C_{4-10}$ alkylene, optionally substituted $C_{2-8}$ alkylene, optionally substituted $C_{4-8}$ alkylene) and optionally substituted hetero $C_{1-10}$ alkylene (e.g., hetero $C_{2-8}$ alkylene, hetero $C_{2-7}$ alkylene, hetero $C_{2-6}$ alkylene). In certain embodiments, each $R^3$ is the same or different and is selected from the group consisting of optionally substituted $C_{4-8}$ alkylene and $-(CH_2CH_2O)_m-$, wherein m is an integer between 1-3. In some embodiments, each $R^3$ is the same or different and is optionally substituted $C_{4-8}$ alkylene. In some embodiments, at least one $R^3$ is optionally substituted heteroalkylene, as described herein, and at least one $R^3$ is optionally substituted alkylene, as described herein.

In some embodiments, n is 25-250,000; 50-250,000; 75-250,000; 100-250,000; 250-250,000; 400-250,000; 500-250,000; 750-250,000; 1,000-250,000; 25-200,000; 25-175,000; 25-150,000; 25-125,000; 25-100,000; or 25-50,000.

In some embodiments, for a compound of Formula (I):

each $R^1$ is the same or different and is selected from the group consisting of optionally substituted alkylene and optionally substituted heteroalkylene;

each $R^2$ is the same or different and is selected from the group consisting of hydrogen and optionally substituted alkyl;

each $R^3$ is the same or different and is selected from the group consisting of optionally substituted alkylene and optionally substituted heteroalkylene; and n is an integer between 25 and 250,000.

In some embodiments, for a compound of Formula (I):
each $R^1$ is the same or different and is $-[C(R'_2)]_g-$;
each $R^2$ is the same or different and is selected from the group consisting of hydrogen and optionally substituted alkyl;
each $R^3$ is the same or different and is selected from the group consisting of optionally substituted $C_{2-10}$ alkylene and optionally substituted hetero $C_{2-8}$ alkylene;
each R' is the same or different and is selected from the group consisting of hydrogen and optionally substituted alkyl;
g is 1, 2, 3, 4, or 5; and
n is an integer between 25 and 250,000.

In some embodiments, for a compound of Formula (I):
each $R^1$ is the same or different and is $-[C(R'_2)]_g-$;
each $R^2$ is the same or different and is selected from the group consisting of hydrogen and optionally substituted alkyl;
each $R^3$ is the same or different and is selected from the group consisting of optionally substituted $C_{4-8}$ alkylene and $-(CH_2CH_2O)_m-$;
each R' is the same or different and is selected from the group consisting of hydrogen and optionally substituted alkyl;
g is 1, 2, 3, 4, or 5;
m is 1, 2, or 3; and
n is an integer between 25 and 250,000.

In some embodiments, the first polymer of Formula (I) comprises the structure:

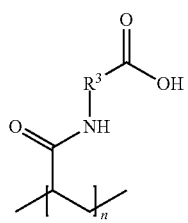

or a pharmaceutically acceptable salt thereof, wherein $R^3$, m, and n are as described herein. For example, each $R^3$ is the same or different and is selected from the group consisting of optionally substituted $C_{4-8}$ alkylene and $-(CH_2CH_2O)_m-$; m is 1, 2, or 3; and n is an integer between 25 and 250,000. In some such embodiments, each $R^3$ is the same or different and is optionally substituted $C_{4-8}$ alkylene.

In some embodiments, the first polymer of Formula (I) comprises the structure:

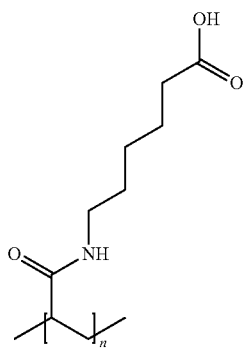

or a pharmaceutically acceptable salt thereof, wherein n is as described herein.

In some embodiments, the first polymer is selected from the group consisting of a polymer of an acryloylaminoalkylene acid monomer, or salts thereof. In certain embodiments, the acryloylaminoalkylene acid monomer is selected from the group consisting of acryloyl-5-aminopentanoic acid, acryloyl-6-aminocaproic acid, acryloyl-7-aminoheptanoic acid, acryloyl-8-aminooctanoic acid, acryloyl-9-aminononoanoic acid, acryloyl-10-aminodecanoic acid, acryloyl-11-aminoundecanoic acid, acryloyl-12-aminododecanoic acid, methacryloyl-5-aminopentanoic acid, methacryloyl-6-aminocaproic acid, methacryloyl-7-aminoheptanoic acid, methacryloyl-8-aminooctanoic acid, methacryloyl-9-aminononoanoic acid, methacryloyl-10-aminodecanoic acid, methacryloyl-11-aminoundecanoic acid, methacryloyl-12-aminododecanoic acid, salts thereof, and combinations thereof.

In certain embodiments, the first polymer is a homopolymer of acryloyl-6-aminocaproic acid or salts thereof.

In some embodiments, the second polymer may comprise Formula (II):

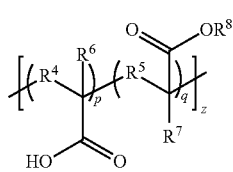

or a pharmaceutically acceptable salt thereof, wherein:
each $R^4$ is the same or different and is selected from the group consisting of optionally substituted alkylene and optionally substituted heteroalkylene;
each $R^5$ is the same or different and is selected from the group consisting of optionally substituted alkylene and optionally substituted heteroalkylene;
each $R^6$ is the same or different and is selected from the group consisting of hydrogen, optionally substituted alkyl, and optionally substituted heteroalkyl;
each $R^7$ is the same or different and is selected from the group consisting of hydrogen, optionally substituted alkyl, and optionally substituted heteroalkyl;
each $R^8$ is the same or different and is optionally substituted alkyl;
p is an integer between 1 and 10;
q is an integer between 1 and 10; and
z is an integer between 1 and 150,000, provided that $(p+q)*z$ is greater than or equal to 20.

In certain embodiments, each $R^4$ is the same or different and is selected from the group consisting of optionally substituted $C_{1-10}$ alkylene (e.g., optionally substituted $C_{1-8}$ alkylene, optionally substituted $C_{1-5}$ alkylene, optionally substituted $C_{1-3}$ alkylene) and optionally substituted hetero $C_{1-10}$ alkylene (e.g., hetero $C_{1-5}$ alkylene, hetero $C_{1-3}$ alkylene). In certain embodiments, each $R^4$ is the same or different and is $-[C(R''_2)]_e-$, wherein each R'' is the same or different and is selected from the group consisting of hydrogen and optionally substituted alkyl and e is 1, 2, 3, 4, or 5. In some instances, e is 1, 2, or 3 (e.g., e is 1 or 2). In some embodiments, at least one (e.g., at least two, each) $R^4$ is optionally substituted heteroalkylene. In some such embodiments, the heteroalkylene may comprise one or more oxygen atoms. In some instances, the heteroalkylene is an alkoxyene. In some embodiments, at least one $R^4$ is optionally substituted heteroalkylene, as described herein, and at least one $R^4$ is optionally substituted alkylene, as described herein.

In certain embodiments, each $R^5$ is the same or different and is selected from the group consisting of optionally substituted $C_{1-10}$ alkylene (e.g., optionally substituted $C_{1-8}$ alkylene, optionally substituted $C_{1-5}$ alkylene, optionally substituted $C_{1-3}$ alkylene) and optionally substituted hetero $C_{1-10}$ alkylene (e.g., hetero $C_{1-5}$ alkylene, hetero $C_{1-3}$ alkylene). In certain embodiments, each $R^5$ is the same or different and is $-[C(R''_2)]_e-$, wherein each R" is the same or different and is selected from the group consisting of hydrogen and optionally substituted alkyl and e is 1, 2, 3, 4, or 5. In some instances, e is 1, 2, or 3 (e.g., e is 1 or 2). In some embodiments, at least one (e.g., at least two, each) $R^4$ is optionally substituted heteroalkylene. In some such embodiments, the heteroalkylene may comprise one or more oxygen atoms. In some instances, the heteroalkylene is an alkoxyene. In some embodiments, at least one $R^5$ is optionally substituted heteroalkylene, as described herein, and at least one $R^5$ is optionally substituted alkylene, as described herein.

In certain embodiments, each $R^6$ is the same or different and is selected from the group consisting of hydrogen and optionally substituted alkyl (e.g., optionally substituted $C_{1-8}$ alkyl, optionally substituted $C_{1-5}$ alkyl, optionally substituted $C_{1-3}$ alkyl). In some embodiments, at least one (e.g., at least two, each) $R^6$ is hydrogen. In some embodiments, at least one $R^6$ is optionally substituted alkyl. In certain embodiments, at least two (e.g., each) $R^6$ are the same or different and are optionally substituted alkyl. In some such embodiments, each $R^6$ is the same or different and is optionally substituted $C_{1-10}$ alkyl (e.g., optionally substituted $C_{1-8}$ alkyl, optionally substituted $C_{1-5}$ alkyl, optionally substituted $C_{1-3}$ alkyl). For example, each $R^6$ may be the same or different and may be methyl or ethyl. In some embodiments, at least one $R^6$ is optionally substituted heteroalkyl. In certain embodiments, at least two (e.g., each) $R^6$ are the same or different and is optionally substituted heteroalkyl.

In certain embodiments, each $R^7$ is the same or different and is selected from the group consisting of hydrogen and optionally substituted alkyl (e.g., optionally substituted $C_{1-8}$ alkyl, optionally substituted $C_{1-5}$ alkyl, optionally substituted $C_{1-3}$ alkyl). In some embodiments, at least one (e.g., at least two, each) $R^7$ is hydrogen. In some embodiments, at least one $R^7$ is optionally substituted alkyl. In certain embodiments, at least two (e.g., each) $R^7$ are the same or different and are optionally substituted alkyl. In some such embodiments, each $R^7$ is the same or different and is optionally substituted $C_{1-10}$ alkyl (e.g., optionally substituted $C_{1-8}$ alkyl, optionally substituted $C_{1-5}$ alkyl, optionally substituted $C_{1-3}$ alkyl). For example, each $R^7$ may be the same or different and may be methyl or ethyl. In some embodiments, at least one $R^7$ is optionally substituted heteroalkyl. In certain embodiments, at least two (e.g., each) $R^7$ are the same or different and is optionally substituted heteroalkyl.

In certain embodiments, each $R^8$ is the same or different and is optionally substituted $C_{1-10}$ alkylene (e.g., optionally substituted $C_{1-8}$ alkylene, optionally substituted $C_{1-5}$ alkylene, optionally substituted $C_{1-3}$ alkylene). For example, each $R^7$ may be the same or different and may be methyl or ethyl.

In some embodiments, p and/or q is 1-9, 1-8, 1-7, 1-6, 1-5, 1-4, 2-10, 2-9, 2-8, 2-7, 2-6, 2-5, or 2-4.

In some embodiments, z is 1-150,000; 25-150,000; 50-150,000; 75-150,000; 100-150,000; 250-150,000; 400-150,000; 500-150,000; 750-150,000; 1,000-150,000; 1-125,000; 1-100,000; 1-75,000; or 25-50,000, provided that (p+q)*z is greater than or equal to 20.

In some embodiments, for a second polymer of Formula (II):

each $R^4$ is the same or different and is optionally substituted alkylene;

each $R^5$ is the same or different and is optionally substituted alkylene;

each $R^6$ is the same or different and is selected from the group consisting of hydrogen and optionally substituted alkyl;

each $R^7$ is the same or different and is selected from the group consisting of hydrogen and optionally substituted alkyl;

each $R^8$ is the same or different and is optionally substituted alkyl p is an integer between 1 and 10;

q is an integer between 1 and 10; and z is an integer between 1 and 150,000, provided that (p+q)*z is greater than or equal to 20.

In some embodiments, for a second polymer of Formula (II):

each $R^4$ the same or different and is $-[C(R''_2)]_e-$;

each $R^5$ is the same or different and is $-[C(R''_2)]_e-$;

each $R^6$ is the same or different and is selected from the group consisting of hydrogen and optionally substituted alkyl;

each $R^7$ is the same or different and is selected from the group consisting of hydrogen and optionally substituted alkyl;

each $R^8$ is the same or different and is optionally substituted alkyl each R" is the same or different and is selected from the group consisting of hydrogen and optionally substituted alkyl;

p is an integer between 1 and 10;

q is an integer between 1 and 10;

e is 1, 2, 3, 4, or 5; and z is an integer between 1 and 150,000, provided that (p+q)*z is greater than or equal to 20.

In some embodiments, the second polymer of Formula (II) comprises the structure:

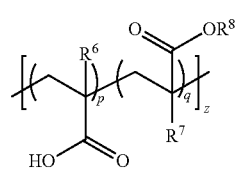

or a pharmaceutically acceptable salt thereof, wherein $R^6$, $R^7$, $R^8$, p, q, and z are as described herein. For example, each $R^7$ is the same or different and is selected from the group consisting of hydrogen and optionally substituted alkyl; each $R^8$ is the same or different and is optionally substituted alkyl; p is an integer between 1 and 10; q is an integer between 1 and 10; and z is an integer between 1 and 150,000, provided that (p+q)*z is greater than or equal to 20.

In some embodiments, the second polymer of Formula (II) comprises the structure:

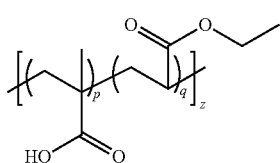

or a pharmaceutically acceptable salt thereof, wherein p, q, and z are as described herein.

In some embodiments, the second polymer comprises poly(methacrylic acid-co-ethyl acrylate) or salts thereof. In some cases, the poly(methacrylic acid-co-ethyl acrylate) has a molar ratio of methacrylic acid monomer units to ethylacrylate monomer units of about 1:1.

In some embodiments, the first polymer may associate with the second polymer via a non-covalent interaction (e.g., hydrogen bonding). In some cases, the non-covalent interaction is a hydrogen bond, ionic interaction, dative bond, and/or a Van der Waals interaction. In some embodiments, the first polymer and the second polymer may interact with each other via at least one hydrogen bond. In some such embodiments, one or more functional group on the first polymer may act as a hydrogen-bond donors and/or acceptors. In such cases, one or more functional group on the second polymer may act as a hydrogen-bond donors and/or acceptors. A hydrogen-bond donor may comprise at least one hydrogen atom configured for associating with a pair of electrons on a hydrogen-bond acceptor to form the hydrogen bond. Non-limiting examples of functional groups on the first and/or second polymers which may form hydrogen bonds include carbonyl groups, amines, hydroxyls, and the like. In some cases, first and/or second polymers may comprise one or more electron-rich or electron-poor moieties. The one or more electron-rich or electron-poor moieties may result in the formation of one or more electrostatic interactions between the first and second polymers.

In some embodiments, the polymer composite is a blend. For example, in certain embodiments, the polymer composite comprises a first polymer (e.g., poly(acryloyl-6-aminocaproic acid)) and a second polymer (e.g., poly(methacrylic acid-co-ethyl acrylate)). In some such embodiments, the weight ratio of the first polymer to the second polymer ranges from about 1:6 to about 6:1. In certain embodiments, the weight ratio of the first polymer to the second polymer is at least about 1:6, at least about 1:5, at least about 1:4, at least about 1:3, at least about 1:2, at least about 1:1, at least about 2:1, at least about 3:1, at least about 4:1, or at least about 5:1. In some embodiments, the weight ratio of the first polymer to the second polymer is less than or equal to about 6:1, less than or equal to about 5:1, less than or equal to about 4:1, 3:1, less than or equal to about 2:1, less than or equal to about 1:1, less than or equal to about 1:2, less than or equal to about 1:3, less than or equal to about 1:4, or less than or equal to about 1:5. Combinations of the above referenced ranges are also possible (e.g., between about 1:6 and about 6:1, between about 1:4 and about 4:1, between about 1:3 and about 3:1, between about 1:2 and about 2:1, between about 1:3 and about 1:1, between about 1:1 and about 3:1). Other ranges are also possible.

In certain embodiments, the polymer composite comprises a mixture of three or more polymers. For example, in some embodiments, the polymer composite comprises a first type of the first polymer, a second type of the first polymer different than the first type, and a first type of the second polymer. Other combinations are also possible.

In some embodiments, the polymer composite is manufactured by forming an aqueous solution of a water soluble salt of the first and second polymers (e.g., the first polymer comprising a structure as in Formula (I) and the second polymer comprising a structure as in Formula (II)). In certain embodiments, the solution comprising the first and second polymers is precipitated with an aqueous acid solution. In some embodiments, the precipitated mixture is de-watered, thereby forming the polymer composite. Those skilled in the art would be configured for selecting suitable methods for de-watering the precipitated mixture including, for example, heating and/or applying vacuum to the precipitated mixture, such that the polymer composite is formed.

In certain embodiments, the polymer composite is manufactured by forming a nonaqueous solution of the first and second polymers in a nonaqueous solvent and evaporating the nonaqueous solvent from the solution of step, thereby forming the polymer composite. In some cases, the polymer composite is contacted with an aqueous solution at a pH of from about 1.0-7.0, thereby forming a polymer composite gel having a water content of less than about 40% by weight.

In some embodiments, nonaqueous solvent is selected from the group consisting of THF, ethanol, isopropanol, butanol, MEK, ethyl acetate, butyl acetate, acetone, methylene chloride, and combinations thereof.

In some embodiments, the polymer composite is a polymer gel with water content no greater than 40 wt %. For example, in some embodiments, the polymer composite has a water content of less than or equal to about 40 wt %, less than or equal to about 30 wt %, less than or equal to about 20 wt %, or less than or equal to about 10 wt %. In some embodiments, the polymer composite has a water content greater than about 5 wt %, greater than about 10 wt %, greater than about 20 wt %, or greater than about 30 wt %. Combinations of the above-referenced ranges are also possible (e.g., between about 5 wt % and about 40 wt %).

In some embodiments, the polymer composite may be cast, molded, and/or cut to have a particular shape, size, and/or volume. In some embodiments, the polymer composite is softened by a nonaqueous solvent and pressure molding the softened polymer composite into a desired shape. In certain embodiments, the polymer composite may be heated to a temperature of less than about 90° C. and pressure molded into a desired shape.

In certain embodiments, the polymer composite may be cast, molded, and/or cut to have a size and/or shape such that it may be retained in an internal orifice of a subject. For example, in some embodiments, an uncompressed cross-sectional dimension of the polymer composite is at least about 2 cm, at least about 4 cm, at least about 5 cm, or at least about 10 cm. In certain embodiments, the uncompressed cross-sectional dimension of the polymer composite is less than or equal to about 15 cm, less than or equal to about 10 cm, less than or equal to about 5 cm, or less than or equal to about 4 cm. Any and all closed ranges that have endpoints within any of the above-referenced ranges are also possible (e.g., between about 2 cm and about 15 cm). Those skilled in the art would be capable of selecting suitable uncompressed cross-sectional dimensions for structures based upon the teachings of this specification for specific orifices of a subject such that the structure is retained.

In certain embodiments, the polymer composite may be bonded to a separate polymer (e.g., in the formation of a structure) by contacting at least a portion of the polymer composite with the separate polymer and heating and/or applying pressure to said contacted polymers to form a bond at the interface. In certain cases, a nonaqueous solution of the polymer composite in a nonaqueous solvent may be contacted with the separate polymer in the nonaqueous solvent, and the nonaqueous solvent removed such that a bond forms at the interface between the polymer composite and the separate polymer. The bond may be an ionic bond, a covalent bond, a hydrogen bond, Van der Waals interactions, and the like. The covalent bond may be, for example, carbon-carbon, carbon-oxygen, oxygen-silicon, sulfur-sulfur, phosphorus-nitrogen, carbon-nitrogen, metal-oxygen, or other covalent bonds. The hydrogen bond may be, for example, between hydroxyl, amine, carboxyl, thiol, and/or similar functional groups.

In some embodiments, the polymer composite is pre-loaded with an active substance such as a therapeutic, diagnostic, and/or enhancement agents. In other embodiments, the polymer composite is loaded with therapeutic, diagnostic, and/or enhancement agents after it is already retained at a location internal to a subject, such as a gastric cavity. In some embodiments, a polymer composite is configured to maintain stability of therapeutic, diagnostic, and/or enhancement agents in a hostile physiological environment (e.g., the gastric environment) for an extended duration. In further embodiments, the polymer composite is configured to control release of therapeutic, diagnostic, and/or enhancement agents with low to no potential for burst release. In some embodiments, the polymer composite is pre-loaded and/or loaded with a combination of active substances. For example, in certain embodiments, the polymer composite comprises one or more, two or more, three or more, or four or more active substances.

Therapeutic, diagnostic, and/or enhancement agents can be loaded into polymer composites and other drug delivery materials via standard methods including, but not limited to, powder mixing, direct addition, solvent loading, melt loading, physical blending, supercritical carbon dioxide assisted, and conjugation reactions such as ester linkages and amide linkages. Release of therapeutic, diagnostic, and/or enhancement agents can then be accomplished through methods including, but not limited to, dissolution of the polymer composite, degradation of the polymer composite, swelling of the polymer composite, diffusion of an agent, hydrolysis, and chemical or enzymatic cleavage of conjugating bonds. In some embodiments, the active substance is covalently bound to the polymer matrix of the polymer composite (e.g., and is released as the polymer matrix degrades).

In certain embodiments, the polymer composite is constructed and arranged to release the active substance from the polymer composite. In certain embodiments, the active substance is designed for release from the polymer composite. Such embodiments may be useful in the context of drug delivery. In other embodiments, the active substance is permanently affixed to the polymer composite. Such embodiments may be useful in molecular recognition and purification contexts. In certain embodiments, the active substance is embedded within the polymer composite. In some embodiments, the active substance is associated with the polymer composite via formation of a bond, such as an ionic bond, a covalent bond, a hydrogen bond, Van der Waals interactions, and the like. The covalent bond may be, for example, carbon-carbon, carbon-oxygen, oxygen-silicon, sulfur-sulfur, phosphorus-nitrogen, carbon-nitrogen, metal-oxygen, or other covalent bonds. The hydrogen bond may be, for example, between hydroxyl, amine, carboxyl, thiol, and/or similar functional groups.

According to some embodiments, the polymer composites described herein are compatible with one or more therapeutic, diagnostic, and/or enhancement agents, such as drugs, nutrients, microorganisms, in vivo sensors, and tracers. In some embodiments, the active substance, is a therapeutic, nutraceutical, prophylactic or diagnostic agent. The active substance may be entrapped within the polymer composite or may be directly attached to one or more atoms in the polymer composite through a chemical bond. In certain embodiments, the active substance is covalently bonded to the polymer composite. In some embodiments, the active substance is bonded to the polymer composite through a carboxylic acid derivative. In some cases, the carboxylic acid derivative may form an ester bond with the active substance.

Agents can include, but are not limited to, any synthetic or naturally-occurring biologically active compound or composition of matter which, when administered to a subject (e.g., a human or nonhuman animal), induces a desired pharmacologic, immunogenic, and/or physiologic effect by local and/or systemic action. For example, useful or potentially useful within the context of certain embodiments are compounds or chemicals traditionally regarded as drugs, vaccines, and biopharmaceuticals, Certain such agents may include molecules such as proteins, peptides, hormones, nucleic acids, gene constructs, etc., for use in therapeutic, diagnostic, and/or enhancement areas, including, but not limited to medical or veterinary treatment, prevention, diagnosis, and/or mitigation of disease or illness (e.g., HMG co-A reductase inhibitors (statins) like rosuvastatin, non-steroidal anti-inflammatory drugs like meloxicam, selective serotonin reuptake inhibitors like escitalopram, blood thinning agents like clopidogrel, steroids like prednisone, antipsychotics like aripiprazole and risperidone, analgesics like buprenorphine, antagonists like naloxone, montelukast, and memantine, cardiac glycosides like digoxin, alpha blockers like tamsulosin, cholesterol absorption inhibitors like ezetimibe, metabolites like colchicine, antihistamines like loratadine and cetirizine, opioids like loperamide, proton-pump inhibitors like omeprazole, antiviral agents like entecavir, antibiotics like doxycycline, ciprofloxacin, and azithromycin, anti-malarial agents, and synthroid/levothyroxine); substance abuse treatment (e.g., methadone and varenicline); family planning (e.g., hormonal contraception); performance enhancement (e.g., stimulants like caffeine); and nutrition and supplements (e.g., protein, folic acid, calcium, iodine, iron, zinc, thiamine, niacin, vitamin C, vitamin D, and other vitamin or mineral supplements).

In some embodiments, the active substance is a radiopaque material such as tungsten carbide or barium sulfate.

In certain embodiments, the active substance is one or more specific therapeutic agents. As used herein, the term "therapeutic agent" or also referred to as a "drug" refers to an agent that is administered to a subject to treat a disease, disorder, or other clinically recognized condition, or for prophylactic purposes, and has a clinically significant effect on the body of the subject to treat and/or prevent the disease, disorder, or condition. Listings of examples of known therapeutic agents can be found, for example, in the United States Pharmacopeia (USP), Goodman and Gilman's The Pharmacological Basis of Therapeutics, 10th Ed., McGraw Hill, 2001; Katzung, B. (ed.) Basic and Clinical Pharmacology, McGraw-Hill/Appleton & Lange; 8th edition (Sep. 21, 2000); Physician's Desk Reference (Thomson Publishing), and/or The Merck Manual of Diagnosis and Therapy, 17th ed. (1999), or the 18th ed (2006) following its publication, Mark H. Beers and Robert Berkow (eds.), Merck Publishing Group, or, in the case of animals, The Merck Veterinary Manual, 9th ed., Kahn, C. A. (ed.), Merck Publishing Group, 2005; and "Approved Drug Products with Therapeutic Equivalence and Evaluations," published by the United States Food and Drug Administration (F.D.A.) (the "Orange Book"). Examples of drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. In certain embodiments, the therapeutic agent is a small molecule. Exemplary classes of therapeutic agents include, but are not limited to, analgesics, anti-analgesics, anti-inflammatory drugs, antipyretics, antidepressants, anti-epileptics, antipsychotic agents, neuroprotective agents, anti-proliferatives, such as anti-cancer agents, antihistamines, antimigraine drugs, hormones, prostaglandins, anti-microbials (including antibiotics, antifungals, antivirals, antiparasitics), antimuscarinics, anxioltyics, bacteriostatics, immunosuppressant agents, sedatives, hypnotics, antipsychotics, bronchodilators, anti-asthma drugs, cardiovascular drugs, anesthetics, anti-coagulants, inhibitors of an enzyme, steroidal agents, steroidal or nonsteroidal anti-inflammatory agents, corticosteroids, dopaminergics, electrolytes, gastro-intestinal drugs, muscle relaxants, nutritional agents, vitamins, parasympathomimetics, stimulants, anorectics and anti-narcoleptics. Nutraceuticals can also be incorporated into the drug delivery device. These may be vitamins, supplements such as calcium or biotin, or natural ingredients such as plant extracts or phytohormones.

In some embodiments, the therapeutic agent is one or more antimalarial drugs. Exemplary antimalarial drugs include quinine, lumefantrine, chloroquine, amodiaquine, pyrimethamine, proguanil, chlorproguanil-dapsone, sulfonamides such as sulfadoxine and sulfamethoxypyridazine, mefloquine, atovaquone, primaquine, halofantrine, doxycycline, clindamycin, artemisinin and artemisinin derivatives. In some embodiments, the antimalarial drug is artemisinin or a derivative thereof. Exemplary artemisinin derivatives include artemether, dihydroartemisinin, arteether and artesunate. In certain embodiments, the artemisinin derivative is artesunate.

Active substances that contain a carboxylic acid group may be directly incorporated into polymeric matrices that contain ester and hydroxyl groups without further modification. Active substances containing an alcohol may first be derivatized as a succinic or fumaric acid monoester and then incorporated into the polymeric matrix. Active substances that contain a thiol may be incorporated into olefin or acetylene-containing matrices through a sulfur-ene reaction. In other embodiments, the one or more agents are non-covalently associated with the polymeric matrices (e.g., dispersed or encapsulated within).

In other embodiments, the active substance is a protein or other biological macromolecule. Such substances may be covalently bound to the polymeric matrix through ester bonds using available carboxylate containing amino acids, or may be incorporated into polymeric material containing olefinic or acetylenic moieties using a thiol-ene type reaction. In some cases, the active substance comprises an amine functional group capable of reacting with an epoxide functional group to form an amide or ester bond. In other embodiments, the active substance is non-covalently associated with the polymeric matrix. In some such embodiments, the active substance may be dispersed or encapsulated within by hydrophilic and/or hydrophobic forces.

In some cases, the partition coefficient of the active substance in the polymer composite can be tuned. For example, if the active substance is hydrophobic, a hydrophobic polymeric material backbone may, in some cases, slow the release into aqueous solution, however, a hydrophilic polymeric material backbone should accelerate it. Additionally, a hydrophilic polymeric material backbone may, in some cases, increase the rate of water absorption into the material, expanding (e.g., swelling) the polymer composite and accelerating release rate. The expansion and dissolution of the material may be increased, in some embodiments, under conditions when free reactive groups contain ionizable moieties that become charged in the presence of aqueous media. In some such embodiments, as the material disintegrates due to ionic repulsion, the rate of release of contents may be increased via diffusion and/or better access to cleavable bonds may be imparted. Those skilled in the art would be capable of selecting suitable methods for determining the partition coefficient of the active substance including, for example, high performance liquid chromatography (HPLC).

The active substance may be associated with the polymeric matrix and/or present in the polymer composite in any suitable amount. In some embodiments, the active substance is present in the polymer composite an amount ranging between about 0.01 wt % and about 50 wt % versus the total polymer composite weight. In some embodiments, the active substance is present in the polymer composite in an amount of at least about 0.01 wt %, at least about 0.05 wt %, at least about 0.1 wt %, at least about 0.5 wt %, at least about 1 wt %, at least about 2 wt %, at least about 3 wt %, at least about 5 wt %, at least about 10 wt %, at least about 20 wt %, at least about 30 wt %, at least about 40 wt % of the total polymer composite weight. In certain embodiments, the active substance is present in the polymer composite in an amount of less than or equal to about 50 wt %, less than or equal to about 40 wt %, less than or equal to about 30 wt %, less than or equal to about 20 wt %, less than or equal to about 10 wt %, less than or equal to about 5 wt %, less than or equal to about 3 wt %, less than or equal to about 2 wt %, less than or equal to about 1 wt %, less than or equal to about 0.5 wt %, less than or equal to about 0.1 wt %, or less than or equal to about 0.05 wt %. Any and all closed ranges that have endpoints within any of the above-referenced ranges are also possible (e.g., between about 0.01 wt % and about 50 wt %). Other ranges are also possible.

Advantageously, certain embodiments of the polymer composites described herein may permit higher concentrations (weight percent) of active substances such as therapeutic agents to be incorporated as compared to other polymers such as certain conventional hydrogels. In some embodiments, the active substance (e.g., the active substance) may be released from the polymer composite. In certain embodiments, the active substance is released by diffusion out of the polymer composite. In some embodiments, the active substance is released by degradation of the polymer composite (e.g., biodegradation, enzymatic degradation, hydrolysis). In some embodiments, the active substance is released from the polymer composite at a particular rate. Those skilled in the art would understand that the rate of release may be dependent, in some embodiments, on the solubility of the active substance in the medium in which the polymer composite is exposed, such as a physiological fluid such as gastric fluid. The ranges and description included related to the release and/or rate of release of the active substance is generally in reference to hydrophilic, hydrophobic, and/or lipophilic active substances in simulated gastric fluid (e.g., as defined in the United States Pharmacopeia (USP)). Simulated gastric fluids are known in the art and those skilled in the art would be capable of selecting suitable simulated gastric fluids based on the teachings of this specification.

In some embodiments, between 0.05 wt % to 99 wt % of the active substance initially contained in a polymer composite is released (e.g., in vivo) between 24 hours and 1 year. In some embodiments, between about 0.05 wt % and about 99.0 wt % of the active substance is released (e.g., in vivo) from the polymer composite after a certain amount of time. In some embodiments, at least about 0.05 wt %, at least about 0.1 wt %, at least about 0.5 wt %, at least about 1 wt %, at least about 5 wt %, at least about 10 wt %, at least about 20 wt %, at least about 50 wt %, at least about 75 wt %, at least about 90 wt %, at least about 95 wt %, or at least about 98 wt % of the active substance associated with the polymer composite is released from the component (e.g., in vivo) within about 24 hours, within 36 hours, within 72 hours, within 96 hours, or within 192 hours. In certain embodiments, at least about 0.05 wt %, at least about 0.1 wt %, at least about 0.5 wt %, at least about 1 wt %, at least about 5 wt %, at least about 10 wt %, at least about 20 wt %, at least about 50 wt %, at least about 75 wt %, at least about 90 wt %, at least about 95 wt %, or at least about 98 wt % of the active substance associated with the polymeric component is released from the component (e.g., in vivo) within 1 day, within 5 days, within 30 days, within 60 days, within 120 days, or within 365 days. For example, in some cases, at least about 90 wt % of the active substance associated with the polymeric component is released from the component (e.g., in vivo) within 120 days.

In some embodiments, the active substance is released from the polymer composite at a particular initial average rate as determined over the first 24 hours of release (the "initial rate") (e.g., release of the active substance at the desired location internally of the subject, such as an internal cavity). In certain embodiments, the active substance is released at an average rate of at least about 1%, at least about 2%, at least about 5%, least about 10%, at least about 20%, at least about 30%, least about 50%, at least about 75%, at least about 80%, at least about 90%, at least about 95%, or at least about 98% of the initial average rate over a 24 hour period after the first 24 hours of release. In some embodiments, the active substance is released at an average rate of less than or equal to about 99%, less than or equal to about 98%, less than or equal to about 95%, less than or equal to about 90%, less than or equal to about 80%, less than or equal to about 75%, less than or equal to about 50%, less than or equal to about %, less than or equal to about 30%, less than or equal to about 20%, less than or equal to about 10%, less than or equal to about 5%, or less than or equal to about 2% of the initial average rate over a 24 hour period after the first 24 hours of release. Any and all closed ranges that have endpoints within any of the above referenced ranges are also possible (e.g., between about 1% and about 99%, between about 1% and about 98%, between about 2% and about 95%, between about 10% and about 30%, between about 20% and about 50%, between about 30% and about 80%, between about 50% and about 99%). Other ranges are also possible.

The active substance may be released at an average rate over at least one selected continuous 24 hour period at a rate of between about 1% and about 99% of the initial rate between 48 hours and about 1 year (e.g., between 48 hours and 1 week, between 3 days and 1 month, between 1 week and 1 month, between 1 month and 6 months, between 3 months and 1 year, between 6 months and 2 years) after the initial release.

For example, in some cases, the active substance may be released at a rate of between about 1% and about 99% of the initial rate on the second day of release, the third day of release, the fourth day of release, the fifth day of release, the sixth day of release, and/or the seventh day of release.

In certain embodiments, burst release of an active substance from the polymer composite is generally avoided. In an illustrative embodiment, in which at least about 0.05 wt % of the active substance is released from the polymer composite within 24 hours, between about 0.05 wt % and about 99 wt % is released during the first day of release (e.g., at the location internally of the subject), and between about 0.05 wt % and about 99 wt % is released during the second day of release. Those skilled in the art would understand that the active substance may be further released in similar amounts during a third day, a fourth day, a fifth day, etc. depending on the properties of the polymer composite and/or the active substance.

In certain embodiments, the active substance may be released with a pulse release profile. For example, in some embodiments, the active substance may be released on the first day after administration and during another 24 hour period such as starting during the third day, the fourth day, or the fifth day, but is not substantially released on other days. Those skilled in the art would understand that other days and/or combinations of pulsing and continuous release are also possible.

The active substance may be released at a relatively constant average rate (e.g., a substantially zero-order average release rate) over a time period of at least about 24 hours. In certain embodiments, the active substance is released at a first-order release rate (e.g., the rate of release of the active substance is generally proportional to the concentration of the active substance) of a time period of at least about 24 hours.

The polymer composite can be used as a material platform. In some embodiments, this material platform features tunable elastomeric properties, is stable in an acidic environment, and/or dissolvable in a more alkali environment. Thus, the polymer composite material platform is compatible with the acidic gastric environment and has the capacity for targeted dissolution in the small intestinal/colonic environment. According to some embodiments, the polymer composite is useful for many applications, including, but not limited to, gastrointestinal structure manufacturing, and gastrointestinal-specific drug delivery with targeted release beyond the pylorus.

A structure bonded with an polymer composite is subject to dissolution in the presence of an alkali environment. Thus, in the case of a gastric structure resident in vivo and comprising an polymer composite, passage of the structure can be induced if the subject ingests an alkali solution (e.g., sodium bicarbonate) to induce the dissolution of the polymer composite to enable breakdown of the structure in accordance with some embodiments.

Certain embodiments comprise administering (e.g., orally) a residence structure comprising the polymer composites described herein to a subject (e.g., a patient) such that the residence structure is retained at a location internal to the subject for a particular amount of time (e.g., at least about 24 hours) before being released. The residence structure may be, in some cases, a gastric residence structure. In some embodiments, the structures and systems described herein comprise one or more polymers configured for high levels of active substances (e.g., a therapeutic agent) loading, high active substance and/or structure stability in acidic environments, mechanical flexibility and strength in an internal orifice (e.g., gastric cavity), and/or rapid dissolution/ degradation in a physiological environment (e.g., intestinal environment). In certain embodiments, the structure has a modular design, combining a material configured for controlled release of therapeutic, diagnostic, and/or enhancement agents with a structural material necessary for gastric residence but configured for controlled and/or tunable degradation/dissolution to determine the time at which retention shape integrity is lost and the structure passes out of the gastric cavity.

In some embodiments, the residence structure comprising the polymer composite has a particular configuration including a particular size and/or shape (e.g., a multi-armed star) in a relaxed state. In certain embodiments, the residence structure may be folded such that it obtains a second, compressed configuration. For example, in some cases, the residence structure may be folded within a capsule in the second configuration such that the residence structure may be delivered orally. The capsule may, in some cases, dissolve such that the residence structure is released at a particular location internal to the subject (e.g., in the stomach) and reversibly obtain the first configuration (i.e. recoil). In some embodiments, the structure is configured to adopt a shape and/or size that slows or prevents further transit in a gastric cavity (e.g., passage from the body of the stomach through the pylorus). In some embodiments, the structure adopts a shape and/or size configured for retention (e.g., gastric residence) upon release from the soluble container and/or soluble retaining element. In some embodiments, the structure is configured for adopting a shape and/or size configured for gastric residence after being stored in its encapsulated shape and/or size for durations greater than 24 hours, including up to about one year. In some embodiments, the mechanical properties of the structure are optimized for safe transient retention in an internal orifice such as the gastric cavity for durations greater than 24 hours, including up to about one year.

According to some embodiments, a residence structure can be configured to maintain safety with low to no potential for intestinal obstruction and/or perforation. Controlled dissolution is important, in some cases, for mitigating the risk of gastrointestinal obstruction. In some embodiments, the structure comprising the polymer composite is designed to dissolve distal to the pylorus. In some embodiments, the polymer composite is attached to and/or incorporated into a structure so that upon degradation/dissolution of the polymer composite, the structure breaks into smaller structures configured for passing through a gastrointestinal tract (e.g., traversing the ileocecal valve) without obstruction. In an illustrative embodiment, the polymer composite does not substantially dissolve and/or degrade when located in the stomach of a subject (e.g., having a pH ranging between about 1 and about 5) and substantially degrades when located (e.g., after passing through the pylorus) in the intestines (e.g., having a pH ranging between about 6.7 and about 7.4).

In some embodiments, the structure (e.g., comprising one or more polymeric components) comprises one or more configurations. For example, in certain embodiments, the structure has a particular configuration such as a defined shape, size, orientation, and/or volume. The structure may comprise any suitable configuration. In some embodiments, the structure has a particular shape as defined by a cross-sectional area of the structure. Non-limiting examples of suitable cross-sectional shapes include square, circles, ovals, polygons (e.g., pentagons, hexagons, heptagons, octagons, nonagons, dodecagons, or the like), tubes, rings, star or star-like (e.g, 3-armed stars, 4-armed stars, 5-armed stars, 6-armed stars, 7-armed stars, 8-armed stars), or the like. Those skilled in the art would be configured for selecting suitable shapes depending on the application (e.g., a star-like shape for gastric retention structures) and based upon the teachings of this specification.

The structure may, in some cases, have an original configuration which may be modified (e.g., deformed) such that the structure obtains a new configuration, different than the original configuration. For example, in some embodiments, the structure has a first configuration and a second configuration, different than the first configuration.

In certain embodiments, the configuration of the structure may be characterized by a largest cross-sectional dimension. In some embodiments, the largest cross-sectional dimension of the first configuration may be at least about 10% less, at least about 20% less, at least about 40% less, at least about 60% less, or at least about 80% less than the largest cross-sectional dimension of the second configuration. In certain embodiments, the largest cross-sectional dimension of the second configuration may be at least about 10% less, at least about 20% less, at least about 40% less, at least about 60% less, or at least about 80% less than the largest cross-sectional dimension of the first configuration. Any and all closed ranges that have endpoints within any of the above referenced ranges are also possible (e.g., between about 10% and about 80%, between about 10% and about 40%, between about 20% and about 60%, between about 40% and about 80%). Other ranges are also possible.

Figure 14:
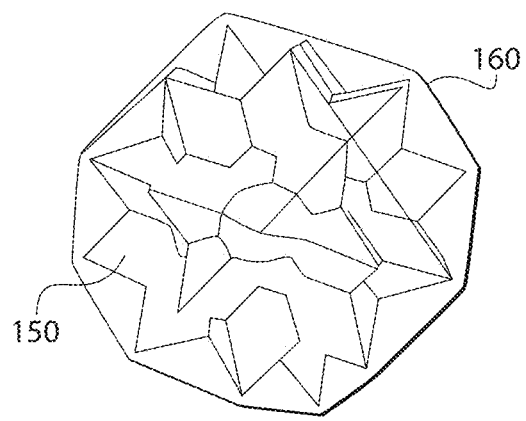
FIG. 14 is a schematic diagram for determining the convex hull volume of a structure, according to one set of embodiments.

In some embodiments, the configuration of the structure may be characterized by a convex hull volume of the structure. The term convex hull volume is known in the art and generally refers to a set of surfaces defined by the periphery of a 3-D object such that the surfaces define a particular volume. For example, as illustrated in FIG. 14, a 3D star-like object 150 has a convex hull volume as defined by convex hull 160. In some embodiments, the convex hull volume of the first configuration may be at least about 10% less, at least about 20% less, at least about 40% less, at least about 60% less, or at least about 80% less than the convex hull volume of the second configuration. In certain embodiments, the convex hull volume of the second configuration may be at least about 10% less, at least about 20% less, at least about 40% less, at least about 60% less, or at least about 80% less than the convex hull volume of the first configuration. Combinations of the above referenced ranges are also possible (e.g., between about 10% and about 80%, between about 10% and about 40%, between about 20% and about 60%, between about 40% and about 80%). Other ranges are also possible.

Those skilled in the art would understand that the differences between the first configuration and the second configuration do not refer to a swelling or a shrinking of the structure (e.g., in the presence of a solvent), but instead refers to a change in shape and/or orientation of at least a portion of the structure (e.g., in the presence of a stimulus such as heat and/or mechanical pressure/compression), although some degree of swelling or shrinking may occur between the two configurations.

In some embodiments, the first configuration is constructed and arranged such that a structure is retained at a location internal of a subject, and the second configuration is constructed and arranged such that the structure may be encapsulated (e.g., for oral delivery of the structure within a capsule). In some cases, the first configuration is sufficiently large such that the structure is retained at a location internal of the subject and the second configuration is sufficiently small such that the structure may fit within a particular size capsule suitable for oral delivery to a subject.

In certain embodiments, the structure may be polymerized and/or cast in a first configuration, mechanically deformed such that the structure obtains a second configuration, and placed in a capsule or restrained by some other containment structure. The structure may be mechanically deformed using any suitable method including, for example, bending, twisting, folding, molding (e.g., pressing the material into a mold having a new shape), expanding (e.g., applying a tensile force to the material), compressing, and/or wrinkling the structure. The structure may maintain the second configuration for any suitable duration prior to stimulation/release. Advantageously, certain embodiments of the structures described herein may be relatively stable in the first and/or second configurations such that the structure may be stored for long periods of time without significant degradation of mechanical properties of the structure. In some embodiments, the structure may be stable under ambient conditions (e.g., room temperature, atmospheric pressure and relative humidity) and/or physiological conditions (e.g., at or about 37° C., in physiologic fluids) for at least about 1 day, at least about 3 days, at least about 7 days, at least about 2 weeks, at least about 1 month, at least about 2 months, at least about 6 months, at least about 1 year, or at least about 2 years. In certain embodiments, the structure has a shelf life of less than or equal to about 3 years, less than or equal to about 2 years, less than or equal to about 1 year, less than or equal to about 1 month, less than or equal to about 1 week, or less than or equal to about 3 days. Any and all closed ranges that have endpoints within any of the above-referenced ranged are also possible (e.g., between about 24 hours and about 3 years, between about 1 week and 1 year, between about 1 year and 3 years). Other ranges are also possible.

In some embodiments, the structure in the second configuration may recoil such that the structure reverts to the first configuration. For example, in some embodiments, the structure in the second configuration is contained within a capsule and delivered orally to a subject. In some such embodiments, the structure may travel to the stomach and the capsule may release the structure from the capsule, upon which the structure obtains (e.g., recoils to) the first configuration.

Medical structures (e.g., implants) fabricated using polymer composites described herein have, according to certain embodiments, one or more of several advantages. For example, in some embodiments, the medical structures (e.g., implants) may be made directly in a molding process, or polymer composite stock may be produced that can be machined, cut, drilled, or otherwise converted into the desired structure.

In a further embodiment, the polymer composite is used to fabricate medical structures. For example, the polymer composite may be used to make partially or fully absorbable biocompatible medical structures, or components thereof. In some cases, the structure to be fabricated is dependent on the mechanical properties of polymer composite. For example, polymer composites that are elastic/flexible may be used to form structures that require such properties to be effective. Elastic and flexible materials are typically those which have a lower degree of crosslinking, which can be achieved by controlling, for example, the bake time of the polymer composite, the polymers reacted to form the composite, and/or the ratio of polymers. In some cases, elastic and flexible properties may be imparted by the incorporation of additional polymers into the polymer composite and/or additives.

Structures that may comprise certain of the polymer composites described herein include, but are not limited to, sutures (e.g., barbed suture, braided suture, monofilament suture, hybrid suture of monofilament and multifilament fibers), braids, ligatures, knitted or woven meshes, knitted tubes, catheters, monofilament meshes, multifilament meshes, patches, wound healing structure, bandage (e.g., wound dressing, burn dressing, ulcer dressing), skin substitute, hemostat, tracheal reconstruction structure, organ salvage structure, dural substitute, dural patch, nerve guide, nerve regeneration or repair structure, hernia repair structure, hernia mesh, hernia plug, structure for temporary wound or tissue support, tissue engineering scaffold, guided tissue repair/regeneration structure, anti-adhesion membrane, adhesion barrier, tissue separation membrane, retention membrane, sling, structure for pelvic floor reconstruction, urethral suspension structure, structure for treatment of urinary incontinence, structure for treatment of vesicoureteral reflux, bladder repair structure, sphincter muscle repair structure, injectable particles, injectable microspheres, bulking or filling structure, bone marrow scaffold, clip, clamp, screw, pin, nail, medullary cavity nail, bone plate, interference screw, tack, fastener, rivet, staple, fixation structure for an implant, bone graft substitute, bone void filler, suture anchor, bone anchor, ligament repair structure, ligament augmentation structure, ligament graft, anterior cruciate ligament repair structure, tendon repair structure, tendon graft, tendon augmentation structure, rotator cuff repair structure, meniscus repair structure, meniscus regeneration structure, articular cartilage repair structure, osteochondral repair structure, spinal fusion structure, structure for treatment of osteoarthritis, viscosupplement, stent, including coronary, cardiovascular, peripheral, ureteric, urethral, urology, gastroenterology, nasal, ocular, or neurology stents and stent coatings, stent graft, cardiovascular patch, catheter balloon, vascular closure structure, intracardiac septal defect repair structure, including but not limited to atrial septal defect repair structures and PFO (patent foramen ovale) closure structures, left atrial appendage (LAA) closure structure, pericardial patch, vein valve, heart valve, vascular graft, myocardial regeneration structure, periodontal mesh, guided tissue regeneration membrane for periodontal tissue, ocular cell implant, imaging structure, cochlear implant, embolization structure, anastomosis structure, cell seeded structure, cell encapsulation structure, controlled release structure, drug delivery structure, plastic surgery structure, breast lift structure, mastopexy structure, breast reconstruction structure, breast augmentation structure (including structures for use with breast implants), breast reduction structure (including structures for removal, reshaping and reorienting breast tissue), structures for breast reconstruction following mastectomy with or without breast implants, facial reconstructive structure, forehead lift structure, brow lift structure, eyelid lift structure, face lift structure, rhytidectomy structure, thread lift structure (to lift and support sagging areas of the face, brow and neck), rhinoplasty structure, structure for malar augmentation, otoplasty structure, neck lift structure, mentoplasty structure, cosmetic repair structure, and structure for facial scar revision.

In a further embodiment, the medical structure is fabricated from a polymer composite having one or more active substances. In one embodiment, the active substance is a therapeutic agent which can reduce pain and/or inflammation, enhance structure attachment in the body, or reduce the likelihood of infection or structure rejection. In a further embodiment, the structure is a stent and the active substance is an agent that prevents restenosis. In another embodiment, the structure is an implantable article and the active substance is an agent for the prevention or suppression of implant rejection and/or promote inflammation to achieve intentional fibrosis for cosmetic purposes. Active substances are described in more detail, above.

As described herein, in some embodiments, the polymer composites may be molded to have a particular shape. In certain embodiments, the polymer composite may be molded to have a particular texture. For example, in some embodiments, the surface of the polymer composite may be rough and/or have particular features which offer advantageous properties as compared to traditional enteric polymers. In certain embodiments, the texture of the polymer composite may be such that it changes (e.g., increases, decreases) the wettability of the composition and/or polymeric material. Wettability may be determined, in some cases, by measuring the contact angle of a droplet of water with the surface of the polymer composite. In certain embodiments, the polymer composite may be textured such that at least a surface of the polymer composite is hydrophobic. In some embodiments, the contact angle of a droplet of water with the polymer composite comprising a textured surface may be between about 80 degrees and about 150 degrees. For example, in some embodiments, the contact angle of a droplet of water with the polymer composite comprising a textured surface may be at least about 80 degrees, at least about 90 degrees, at least about 95 degrees, at least about 100 degrees, at least about 110 degrees, or at least about 120 degrees. In certain embodiments, the contact angle of a droplet of water with the polymer composite comprising a textured surface may be less than or equal to about 150 degrees, less than or equal to about 120 degrees, less than or equal to about 110 degrees, less than or equal to about 100 degrees, less than or equal to about 95 degrees, or less than or equal to about 90 degrees. Combinations of the above referenced ranges are also possible (e.g., between about 80 degrees and about 150 degrees). Other ranges are also possible.

In some embodiments, the polymer composite comprising a therapeutic agent as described herein may increase the stability and/or the shelf life of the therapeutic agent as compared to traditional drug-delivery materials.

In another embodiment, the polymer composite is provided as a kit to an end-user.

Any terms as used herein related to shape, orientation, alignment, and/or geometric relationship of or between, for example, one or more articles, compositions, structures, materials and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape—such as, round, square, circular/circle, rectangular/rectangle, triangular/triangle, cylindrical/cylinder, elipitical/elipse, (n)polygonal/(n)polygon, etc.; angular orientation—such as perpendicular, orthogonal, parallel, vertical, horizontal, collinear, etc.; contour and/or trajectory—such as, plane/planar, coplanar, hemispherical, semi-hemispherical, line/linear, hyperbolic, parabolic, flat, curved, straight, arcuate, sinusoidal, tangent/tangential, etc.; surface and/or bulk material properties and/or spatial/temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described.

The term "subject," as used herein, refers to an individual organism, for example, a human or an animal. In some embodiments, the subject is a mammal (e.g., a human, a non-human primate, or a non-human mammal), a vertebrate, a laboratory animal, a domesticated animal, an agricultural animal, or a companion animal. In some embodiments, the subject is a human. In some embodiments, the subject is a rodent, a mouse, a rat, a hamster, a rabbit, a dog, a cat, a cow, a goat, a sheep, or a pig.

The term "electrophile," as used herein, refers to a functionality which is attracted to an electron and which participates in a chemical reaction by accepting an electron pair in order to bond to a nucleophile.

The term "nucleophile" as used herein, refers to a functionality which donates an electron pair to an electrophile in order to bond to a electrophile.

As used herein, the term "react" or "reacting" refers to the formation of a bond between two or more components to produce a stable, isolable compound. For example, a first component and a second component may react to form one reaction product comprising the first component and the second component joined by a covalent bond. The term "reacting" may also include the use of solvents, catalysts, bases, ligands, or other materials which may serve to promote the occurrence of the reaction between component(s). A "stable, isolable compound" refers to isolated reaction products and does not refer to unstable intermediates or transition states.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The alkyl groups may be optionally substituted, as described more fully below. Examples of alkyl groups include, but are not limited to, methyl, ethyl, propyl, isopropyl, butyl, isobutyl, tert-butyl, 2-ethylhexyl, cyclopropyl, cyclobutyl, cyclopentyl, cyclohexyl, and the like. "Heteroalkyl" groups are alkyl groups wherein at least one atom is a heteroatom (e.g., oxygen, sulfur, nitrogen, phosphorus, etc.), with the remainder of the atoms being carbon atoms. Examples of heteroalkyl groups include, but are not limited to, alkoxy, poly(ethylene glycol)-, alkyl-substituted amino, tetrahydrofuranyl, piperidinyl, morpholinyl, etc.

The terms "alkenyl" and "alkynyl" refer to unsaturated aliphatic groups analogous to the alkyl groups described above, but containing at least one double or triple bond respectively. The "heteroalkenyl" and "heteroalkynyl" refer to alkenyl and alkynyl groups as described herein in which one or more atoms is a heteroatom (e.g., oxygen, nitrogen, sulfur, and the like).

The term "aryl" refers to an aromatic carbocyclic group having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl), all optionally substituted. "Heteroaryl" groups are aryl groups wherein at least one ring atom in the aromatic ring is a heteroatom, with the remainder of the ring atoms being carbon atoms. Examples of heteroaryl groups include furanyl, thienyl, pyridyl, pyrrolyl, N lower alkyl pyrrolyl, pyridyl N oxide, pyrimidyl, pyrazinyl, imidazolyl, indolyl and the like, all optionally substituted.

The terms "amine" and "amino" refer to both unsubstituted and substituted amines, e.g., a moiety that can be represented by the general formula: N(R')(R")(R''') wherein R', R", and R''' each independently represent a group permitted by the rules of valence.

The terms "acyl," "carboxyl group," or "carbonyl group" are recognized in the art and can include such moieties as can be represented by the general formula:

wherein W is H, OH, O-alkyl, O-alkenyl, or a salt thereof. Where W is O-alkyl, the formula represents an "ester." Where W is OH, the formula represents a "carboxylic acid." In general, where the oxygen atom of the above formula is replaced by sulfur, the formula represents a "thiolcarbonyl" group. Where W is a S-alkyl, the formula represents a "thiolester." Where W is SH, the formula represents a "thiolcarboxylic acid." On the other hand, where W is alkyl, the above formula represents a "ketone" group. Where W is hydrogen, the above formula represents an "aldehyde" group.

As used herein, the term "heteroaromatic" or "heteroaryl" means a monocyclic or polycyclic heteroaromatic ring (or radical thereof) comprising carbon atom ring members and one or more heteroatom ring members (such as, for example, oxygen, sulfur or nitrogen). Typically, the heteroaromatic ring has from 5 to about 14 ring members in which at least 1 ring member is a heteroatom selected from oxygen, sulfur, and nitrogen. In another embodiment, the heteroaromatic ring is a 5 or 6 membered ring and may contain from 1 to about 4 heteroatoms. In another embodiment, the heteroaromatic ring system has a 7 to 14 ring members and may contain from 1 to about 7 heteroatoms. Representative heteroaryls include pyridyl, furyl, thienyl, pyrrolyl, oxazolyl, imidazolyl, indolizinyl, thiazolyl, isoxazolyl, pyrazolyl, isothiazolyl, pyridazinyl, pyrimidinyl, pyrazinyl, triazinyl, triazolyl, pyridinyl, thiadiazolyl, pyrazinyl, quinolyl, isoquinolyl, indazolyl, benzoxazolyl, benzofuryl, benzothiazolyl, indolizinyl, imidazopyridinyl, isothiazolyl, tetrazolyl, benzimidazolyl, benzoxazolyl, benzothiazolyl, benzothiadiazolyl, benzoxadiazolyl, carbazolyl, indolyl, tetrahydroindolyl, azaindolyl, imidazopyridyl, qunizaolinyl, purinyl, pyrrolo[2,3]pyrimidyl, pyrazolo[3,4]pyrimidyl, benzo(b)thienyl, and the like. These heteroaryl groups may be optionally substituted with one or more substituents.

The term "substituted" is contemplated to include all permissible substituents of organic compounds, "permissible" being in the context of the chemical rules of valence known to those of ordinary skill in the art. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" must still comprise the phenyl moiety and cannot be modified by substitution, in this definition, to become, e.g., a heteroaryl group such as pyridine. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, alkyl, aryl, aralkyl, cyclic alkyl, heterocycloalkyl, hydroxy, alkoxy, aryloxy, perhaloalkoxy, aralkoxy, heteroaryl, heteroaryloxy, heteroarylalkyl, heteroaralkoxy, azido, amino, halogen, alkylthio, oxo, acyl, acylalkyl, carboxy esters, carboxyl, carboxamido, nitro, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, alkoxyalkyl, perhaloalkyl, arylalkyloxyalkyl, and the like.

As used herein, the term "network" refers to a three dimensional substance having oligomeric or polymeric strands interconnected to one another by crosslinks.

As used herein, the term "strand" refers to an oligomeric or polymeric chain of one monomer unit, or an oligomeric or polymeric chain of two or more different monomer units.

As used herein, the term "backbone" refers to the atoms and bonds through which the monomer units are bound together. As used herein, the term "prepolymer" refers to oligomeric or polymeric strands which have not undergone crosslinking to form a network.

As used herein, the term "crosslink" refers to a connection between two strands. The crosslink may either be a chemical bond, a single atom, or multiple atoms. The crosslink may be formed by reaction of a pendant group in one strand with the backbone of a different strand, or by reaction of one pendant group with another pendant group. Crosslinks may exist between separate strand molecules, and may also exist between different points of the same strand.

As used herein, the term "active substance" refers to a compound or mixture of compounds which causes a change in a biological substrate. Exemplary classes of active substances in the medical and biological arts include therapeutic, prophylactic and diagnostic agents. The active substance may be a small molecule drug, a vitamin, a nutrient, a biologic drug, a vaccine, a protein, an antibody or other biological macromolecule. The active substance may be a mixture of any of the above listed types of compounds.

"Immunosuppressive agent" refers to an agent that inhibits or prevents an immune response to a foreign material in a subject. Immunosuppressive agents generally act by inhibiting T-cell activation, disrupting proliferation, or suppressing inflammation.

As used herein, the terms "oligomer" and "polymers" each refer to a compound of a repeating monomeric subunit. Generally speaking, an "oligomer" contains fewer monomeric units than a "polymer." Those of skill in the art will appreciate that whether a particular compound is designated an oligomer or polymer is dependent on both the identity of the compound and the context in which it is used.

One of ordinary skill will appreciate that many oligomeric and polymeric compounds are composed of a plurality of compounds having differing numbers of monomers. Such mixtures are often designated by the average molecular weight of the oligomeric or polymeric compounds in the mixture. As used herein, the use of the singular "compound" in reference to an oligomeric or polymeric compound includes such mixtures.

As used herein, reference to any oligomeric or polymeric material without further modifiers includes said oligomeric or polymeric material having any average molecular weight. For instance, the terms "polyethylene glycol" and "polypropylene glycol," when used without further modifiers, includes polyethylene glycols and polypropylene glycols of any average molecular weight.

As used herein, the term "Michael acceptor" refers to a functional group having a carbon-carbon double or triple bond in which at least one of the carbon atoms is further bonded to a carbonyl group or carbonyl analogs such as imine, oxime, and thiocarbonyl. The reaction between a Michael acceptor and nucleophile results in the formation of a covalent bond between the nucleophile and the carbon atom not directly connected to the carbonyl group or carbonyl analog. The reaction between a Michael acceptor and a nucleophile may be called a "Michael addition."

The term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The term "alkoxy" refers to an alkyl group, as defined above, having an oxygen atom attached thereto. Representative alkoxy groups include methoxy, ethoxy, propyloxy, and tert-butoxy. An "ether" is two hydrocarbons covalently linked by an oxygen.

The term "alkylthio" refers to an alkyl group, as defined above, having a sulfur atom attached thereto. In some embodiments, the "alkylthio" moiety is represented by one of —S-alkyl, —S-alkenyl, and —S-alkynyl. Representative alkylthio groups include methylthio and ethylthio.

The term "amido" is art-recognized as an amino substituted by a carbonyl group.

The term "aralkyl", as used herein, refers to an alkyl group substituted with an aryl group. The term "heteroaralkyl", as used herein, refers to an alkyl group substituted with a heteroaryl group.

The term "heteroatom" as used herein means an atom of any element other than carbon or hydrogen. Examplary heteroatoms are nitrogen, oxygen, and sulfur.

As used herein, the term "thiol" means —SH; the term "hydroxyl" means —OH; and the term "sulfonyl" means —SO$_2$—.

As used herein the term "oxo" refers to a carbonyl oxygen atom.

As used herein, the term "alkaloid" refers to a naturally occurring organic compound containing at least one non-peptidic nitrogen atom.

EXAMPLES

The following examples are intended to illustrate certain embodiments of the present invention, but do not exemplify the full scope of the invention.

Example 1—Preparation of Polymer Gel as Enteric Elastomer (EE)

FIGS. 1A-1D depict a proposed supramolecular network structure of the EE polymer gel. The EE consists of two synthetic macromolecules, poly(acryloyl-6-aminocaproic acid) (PA6ACA, $M_n$=61,600-112,700. $M_w$=347,300-466,300, FIGS. 6A-6D) and poly(methacrylic acid-co-ethyl acrylate) (EUDRAGIT® L100-55, $M_n$=72,300. $M_w$=241,000). L100-55 is a pharmaceutical grade enteric polymer from Evonik Industries. PA6ACA, is structurally similar to traditional enteric polymers (e.g. L100-55, cellulose acetate succinate and hydroxyl propyl methyl cellulose phthalate). PA6ACA has side chains of sufficient length for the terminal carboxyl groups to be flexible and accessible allowing the formation of intermolecular hydrogen bonds as shown in FIG. 1A In the acidic environment when carboxyl groups are not deprotonated, inter-chain hydrogen bonds between carboxyl groups and amide units on PA6ACA and L100-55 provide a loosely cross-linked supramolecular network with water trapped inside that may contribute to the elastic property of the materials. In neutral or alkali aqueous environments, the carboxyl groups are deprotonated, eliminating the intermolecular hydrogen bonds, resulting in rapid dissolution.

Figure 1B:
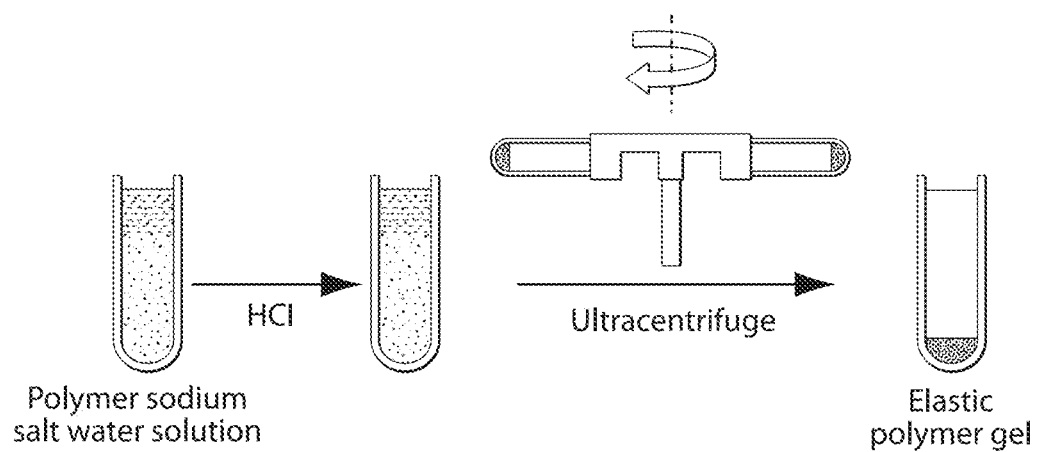
FIG. 1B is a diagram of the manufacturing process of a polymer composite, according to one set of embodiments.

EEs with various compositions and properties were synthesized by co-precipitation of a solution of PA6ACA sodium salt and L 100-55 sodium salt in polymer weight ratios of 1:0, 1:1, and 1:2 with the addition of 6 M HCl solution and compacting by ultracentrifugation (FIG. 1B).

To a well-mixed solution containing 1 g PA6ACA sodium salt, 0.853 g of poly(methacylic acid-co-ethyl acrylate) (EUDRAGIT® L 100-55) and 0.183 g NaOH dissolved in 45 mL nanopure water, a solution of 5 mL of 6 M HCl (diluted from ACS grade concentrated 37% HCl) was quickly added. The mixture was put on the vortex shaker for 5 min, then transferred into thick-wall centrifuge tubes (Beckman Coulter Inc.) and centrifuged in a Beckman Coulter Ultracentrifuge (Avanti® J-26 XP) using an SW 32 Ti rotor at 32,000 rpm for 2 h at 20° C. The resulting enteric elastic polymer gels with PA6ACA/L100-55 ratio 1:1 were extracted from the bottom of the ultracentrifuge tube.

Figure 1C:
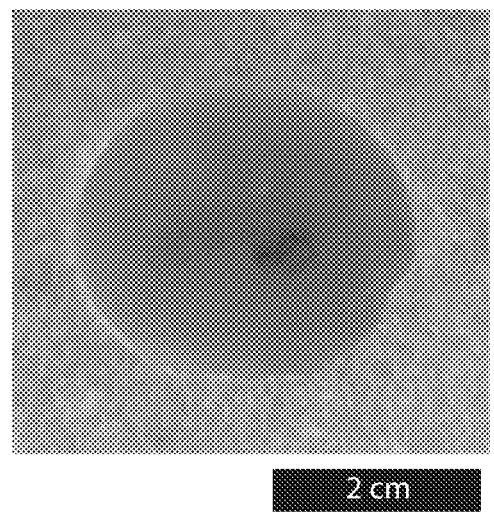
FIG. 1C is a photograph of a polymer composite, according to one set of embodiments.

The co-precipitation and ultracentrifugation process yielded macroscopically homogeneous materials with tough elastic properties and relatively low water contents (<35%, measurement method in supporting information). FIG. 1C shows a typical piece of EE taken from the ultracentrifuge tube (PA6ACA:L100-55 1:2). EE could be generally easily cut into various shapes for the construction of structures or mechanical characterizations. In preliminary mechanical testing (PA6ACA:L100-55 1:2 as shown in FIG. 1D), a cuboid-shape was pulled to three times its original length and fully recovered its shape 5 minutes (FIG. 1D, bottom) after the external force was removed, demonstrating the desired elastic property without material fatigue.

Figure 1D:
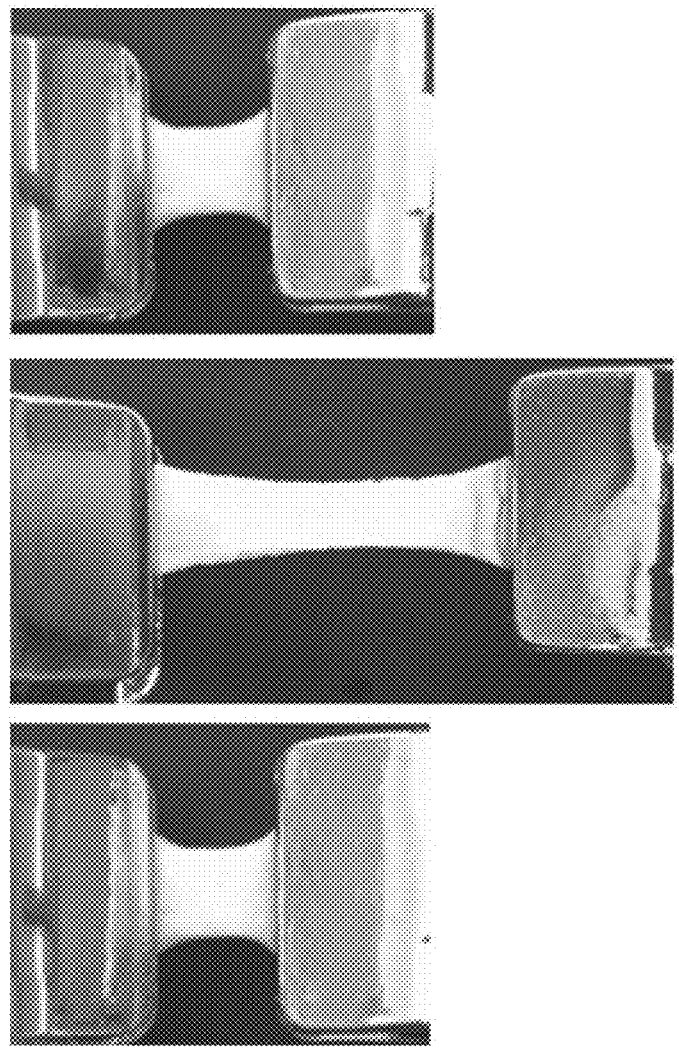
FIG. 1D is a series of photographs of tensile deformation of a polymer composite, according to one set of embodiments.

In FIG. 1D, images of stretch and recovery testing of a 1.5 cm piece of polymer gel with PA6ACA:L100-55=1:2 are shown.

Example 2—Characterization of EE

To better understand the structure-property relationship of EEs with various PA6ACA to L100-55 ratios, the nanostructure, morphology, cytotoxicity, swelling, mechanical and enteric properties of these materials were characterized. At the molecular level, the hydrogen-bonding network of EEs was characterized by using small angle X-ray scattering (SAXS) and infrared (IR) spectroscopy.

SAXS experiments were conducted by DND-CAT of the Advanced Photon Source at Argonne National Laboratory. X-rays of wavelength $\lambda=0.73$ Å were used and each measurement was performed at room temperature using three different sample-to-detector distances (0.2, 1.0, and 7.5 m) to cover an q-range of $0.0026<q<4.4$ Å$^{-1}$, where $q=(4\pi/\lambda)\sin(\theta/2)$ is the magnitude of the scattering vector and $\theta$ is the scattering angle. Gel samples were prepared into a disk shape and fixed vertically to have the x-ray beam pass through the center of the wet samples. Samples were approximately 1.0 mm thick and 3.0 cm in diameter.

Figure 2A:
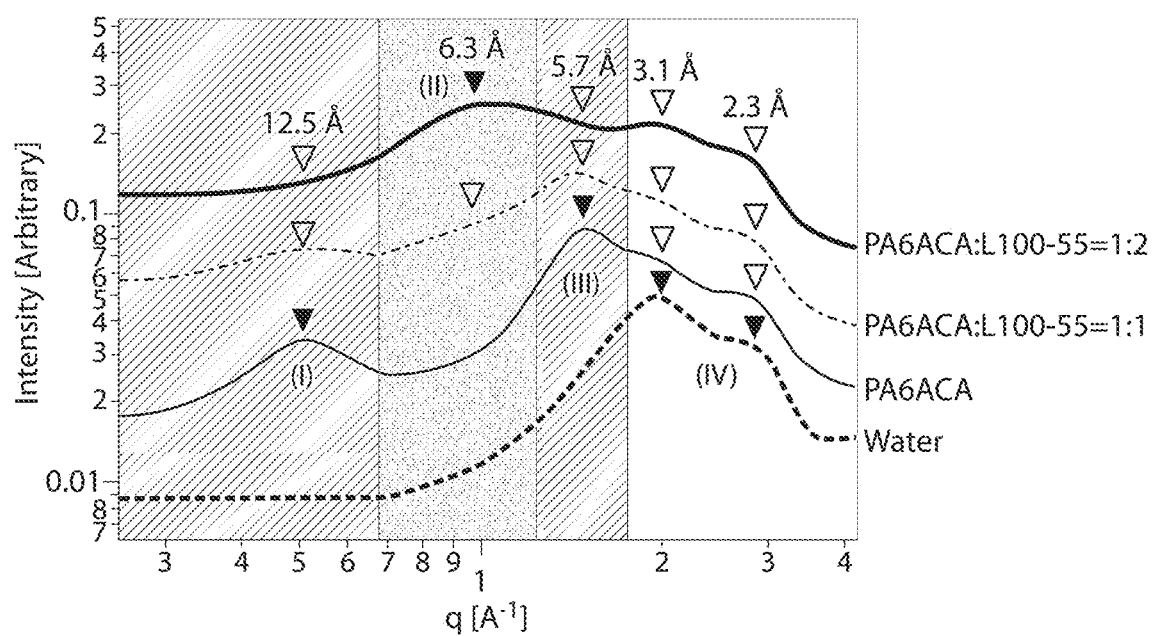
FIG. 2A is a plot of SAXS for a polymer composite, according to one set of embodiments.
Figure 2B:
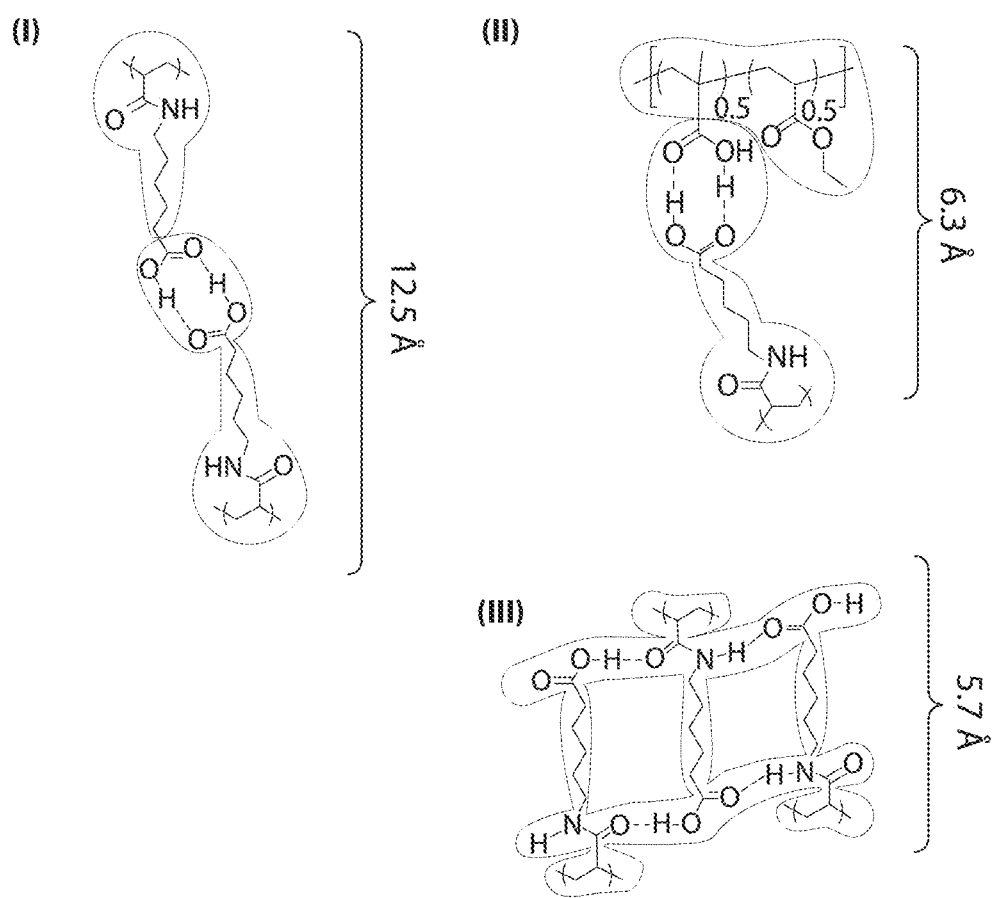
FIG. 2B is a schematic of carboxyl groups on various components of a polymer composite interacting with the opposing carboxyl groups in the polymer composite, according to one set of embodiments.

The scattering profile of PA6ACA gel (FIG. 2A) presents four broad peaks. Two peaks were founds in the higher q-region corresponding to periodic distances of around 3.1 Å and 2.3 Å which were also found in pure water and thus can be attributed to hydrogen-bonding (defined as type IV) between $H_2O$ molecules in the gel. The other two peaks in the lower q-region of SAXS profile represent two distinct periodic distances of 12.5 Å and 5.7 Å, which can be assigned to two co-existing hydrogen-bonding configurations between PA6ACA molecules in the gel, the face-on configuration (type I) and the interleaved configuration (type III), respectively (FIG. 2B). The formation of the two PA6ACA hydrogen-bonding configurations was further supported by IR spectroscopy. When blending PA6ACA with L100-55 in the gel, a new peak appeared in the intermediate q-region (6.3 Å) of SAXS profile, suggesting the formation of a new hydrogen-bonding configuration (type II, FIG. 2B) between PA6ACA and L100-55. Increasing the content of L100-55 in the polymer gels resulted in a relative increase in peak (II) with reduction of peaks (I) and (III) in the SAXS profiles.

Scanning electron microscopy (SEM) was employed to study the microstructure of EEs. As revealed by SEM images of lyophilized gels (FIG. 2C) of three formulations of EE demonstrated porosity in the micrometer range with higher blending ratio of L100-55 correlating with decreasing pore size. The water content decreased from 31.6±3.8% in PA6ACA itself, to 27.7±4.6% in the EE with ratio 1:1, and to 26.4±3.5% in the EE with ratio 1:2, which is consistent with the SEM porosity findings.

The elastic and enteric properties of the EEs were also tested. The mechanical properties and the way in which these are influenced by the blending ratio of PA6ACA to L100-55 were studied using immersion tensile-stress testing in simulated gastric fluid (SGF) at 37° C.

MTS Synergie 400 Tensile Test Machine equipped with a circulating and heating Bionix Mini Bath and an electronic temperature probe was used for the immersion tensile testing. For testing, EEs were cut in about 2 mm×2 mm×20 mm pieces, and held by wedge action grips, exposing 6-12 mm for the testing. SGF at 37° C. was added into the bath and EEs were allowed to equilibrate in SGF for 10 min before pulling. The stretch rate was set to 10 mm·min$^{-1}$. EEs were submerged in SGF during the whole testing process until the fracture.

Figure 2C:
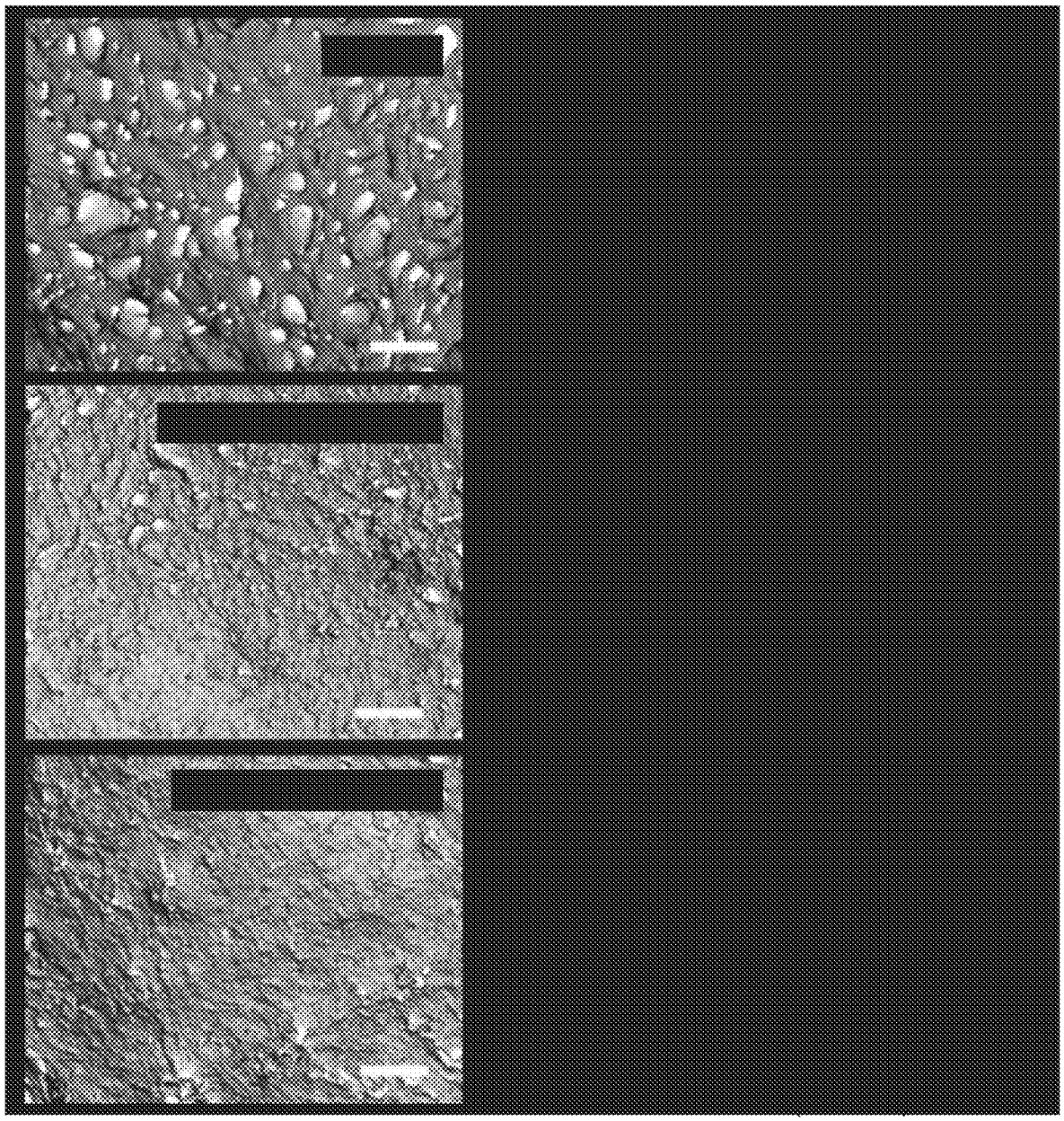
FIG. 2C is an SEM image of dried polymer composites of varying composition, with corresponding true stress-strain plots for each composite, according to one set of embodiments.

With increasing amount of L100-55, the Young's modulus and tensile strength increased, while the strain decreased from 1207% strain in pure PA6ACA and 1230% strain in the EE with the ratio 1:1 to 943% in the EE with the ratio 1:2 (FIG. 2C). The stress-strain test suggests that mechanical properties of EEs can be engineered by tuning the blending ratio of PA6ACA and L100-55. The pH-dependent dissolution properties of EEs were evaluated in simulated gastric fluid (SGF, pH=~1.2) and simulated intestinal fluid (SW, pH=~6.8). To measure dissolution, EEs were cut into ~1 cm$^3$ sized cubes and submerged in either 40 mL SGF or SIF in a 50 mL VWR centrifuge tube. 6 replicates for each time point and condition were incubated at 37° C. on a shaker plate at 250 rpm. The solutions were exchanged with fresh SGF or SIF every 12 hours. At each time point, cubes were lyophilized for 48 hours before weighing. The remaining mass percentage equals the ratio of remaining dried weight to initial dried weight.

Figure 2D:
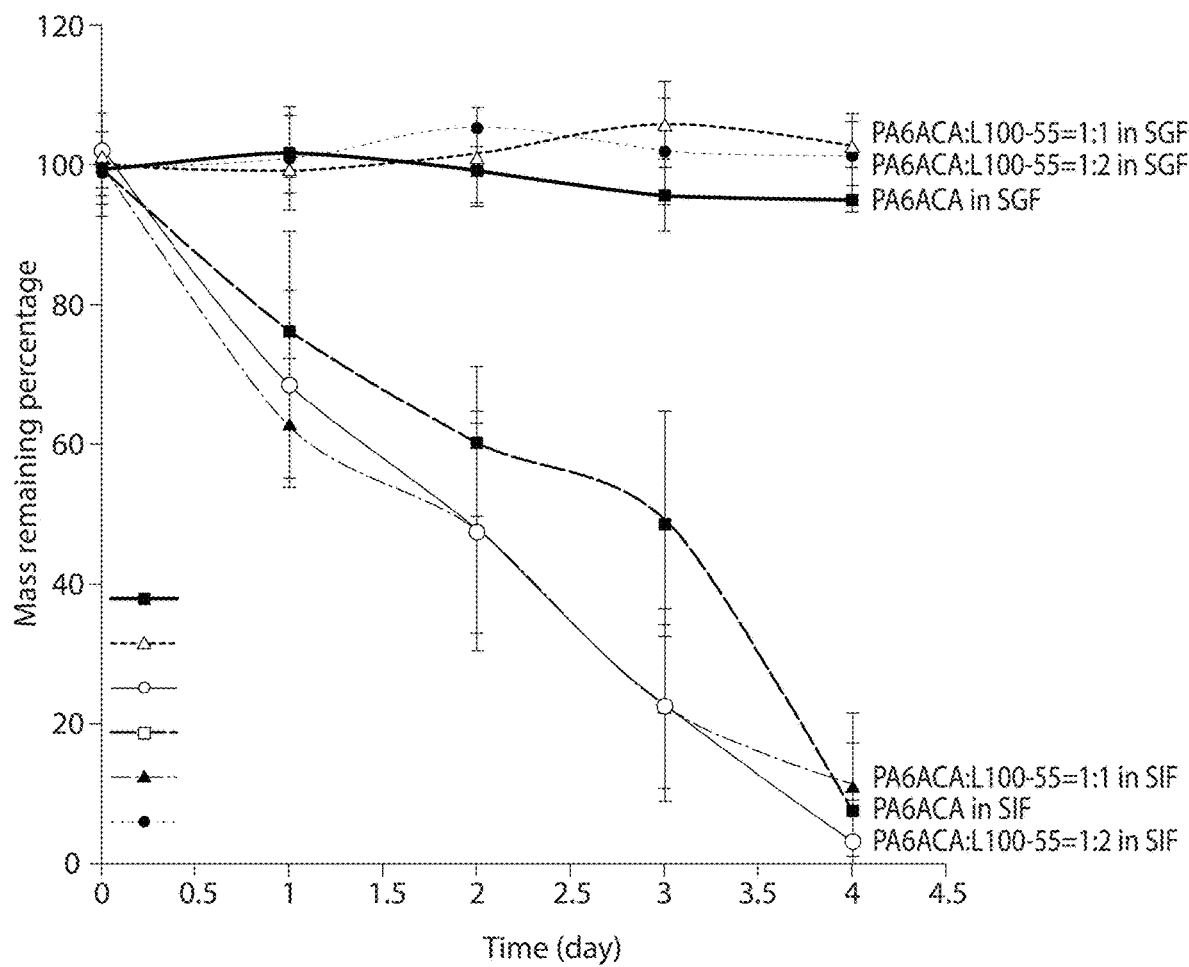
FIG. 2D is a plot of dissolution of polymer composites of varying composition, according to one set of embodiments.
Figure 7:
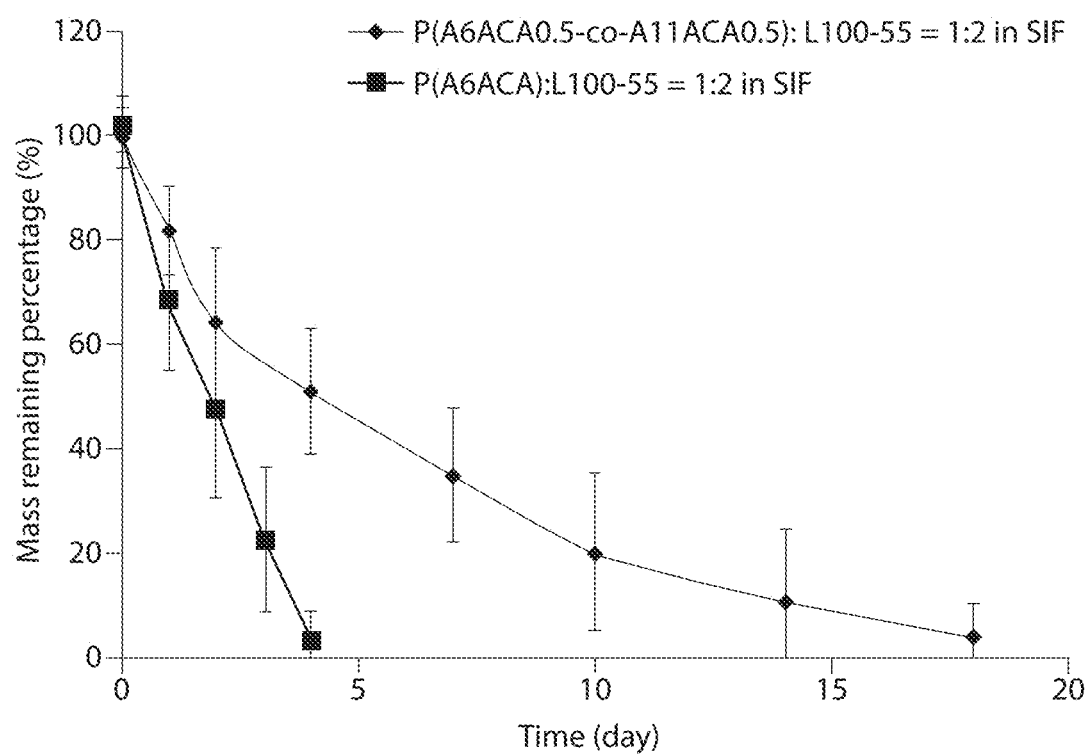
FIG. 7 is a plot of dissolution of polymer composites in simulated intestinal fluid (SIF), according to one set of embodiments.

As shown in FIG. 2D, all three formulations of EEs showed long-term stability in SGF without detectable mass loss over 4 days. In contrast, within the same period of time, all three EEs were nearly dissolved in simulated intestinal fluid (SIF) in a pseudo-zero order manner with similar dissolution rates. To further modulate the enteric properties of EEs, a copolymer was synthesized of N-acryloyl 6-aminocaproic acid (A6ACA) and the more hydrophobic monomer N-acryloyl 11-aminoundecanoic acid (A11AUA) creating P(A6ACA$_{0.5}$-coA11AUA$_{0.5}$) (FIGS. 6A-6D, $M_n$=82,300-170,600. $M_w$=358,400-655,900). This copolymer was blended with L100-55 at a weight ratio of 1:2 resulting in a material that completely dissolved in SIF in 18 days (FIG. 7). Therefore, modulating polymer gel compositions by physical blending or chemical copolymerization, both elastic and/or enteric properties of EEs could be adjusted.

Figure 8:
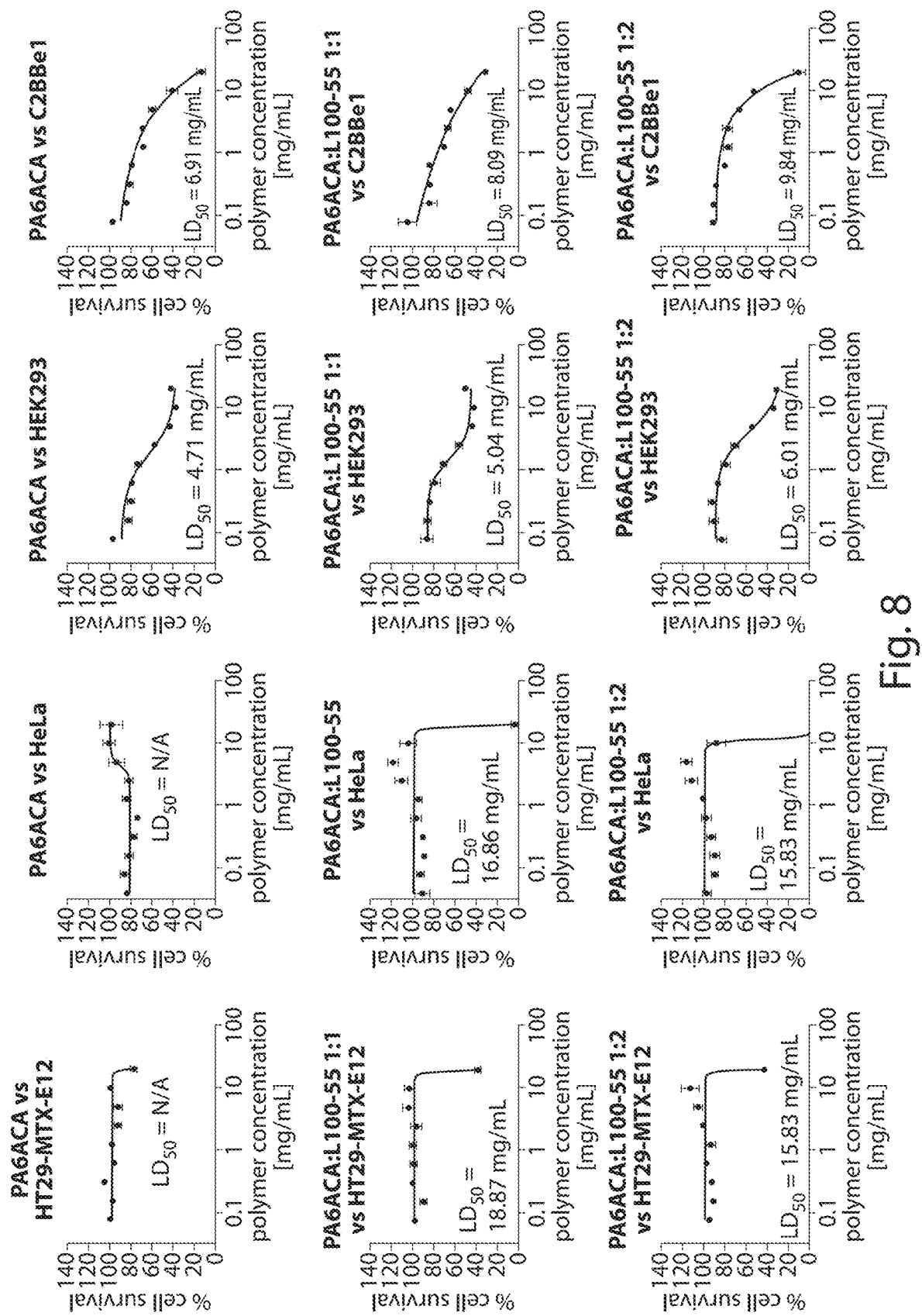
FIG. 8 shows plots of cytotoxicity studies of various polymer composites, according to some embodiments.

To evaluate the biocompatibility and biosafety of EEs, EE sodium salt forms were tested for their cytotoxicity towards multiple cell lines, including HeLa, HEK293 and the intestinal lines Caco-2 (C2BBe1 clone) and HT29-MTX-E12 (FIG. 8).

To conduct the cytotoxicity study, PA6ACA sodium salt and L100-55 were dissolved in an aqueous NaOH solution. Subsequently the pH was adjusted to 7.0 using 1 M HCl. The final polymer solution was diluted with Dulbecco's Modified Eagle Medium (DMEM) (Life Technologies) to 100 mg/mL before testing. Cytotoxicity was tested on HeLa, HEK293, C2BBe1 (ATCC) and HT29-MTX-E12 cells (Public Health England) by seeding them in a 96-well plate at a density of 6×10$^3$, 16×10$^3$, 16×10$^3$ and 2×10$^4$ cells/well respectively. HeLa and HEK293 cells were cultured in 100 µL DMEM containing 1% non-essential amino acids, 10% fetal bovine serum (FBS) and 1% penicillin-streptomycin solution (Life Technologies) per well. C2BBe1 and HT29-MTX-E12 cells were cultured in the same medium but was additionally supplemented with 4 mg/mL human transferrin (Life Technologies). Cells were kept in culture for 3 days before replacing the medium, to which the dissolved aqueous polymer solutions were added (final concentrations of polymers ranged from 0.078-20 mg/mL). After 72 h, cytotoxicity was quantified by adding 10 µL alamarBlue reagent (Life Technologies) to each well. The contents were mixed well and then allowed to incubate at 37° C. for 1 h. Absorbance at 570 nm was recorded on an Infinite M200Pro (Tecan) using 600 nm as reference wavelength. A positive control was provided by lysing cells with 1% Tween-20 and cells that were not subject to any polymer provided a negative control. Cell viability was calculated by the following equation: Cell viability (%)=100×(Absorbance$_{(sample)}$−Absorbance$_{(positive\ control)}$)/(Absorbance$_{(negative\ control)}$−Absorbance$_{(positive\ control)}$).

No significant cytotoxicity was observed for all three formulations of EEs over a wide range of concentrations from 0.078-20 mg/mL at the end of a 72 h incubation period. The observed cytotoxicity at very high concentrations (LD$_{50}$ above 4.71 mg/mL) may be due to changes in pH or viscosity of cell culture medium after dissolving a large amount of high molecular weight polymer sodium salts. EEs were further evaluated for swelling behavior in several commonly ingested fluids including vegetable oil and ethanol. EEs did not swell and maintained their integrity in acidic aqueous solutions (pH≤5.0), and in an acidic solution mixed with 10 wt % vegetable oil (see supporting information). PA6ACA was evaluated for its ability to absorb ethanol. PA6ACA did not swell noticeably in 10% ethanol (FIG. 9) supporting the compatibility of this family of materials with common components of diets.

Figure 9:
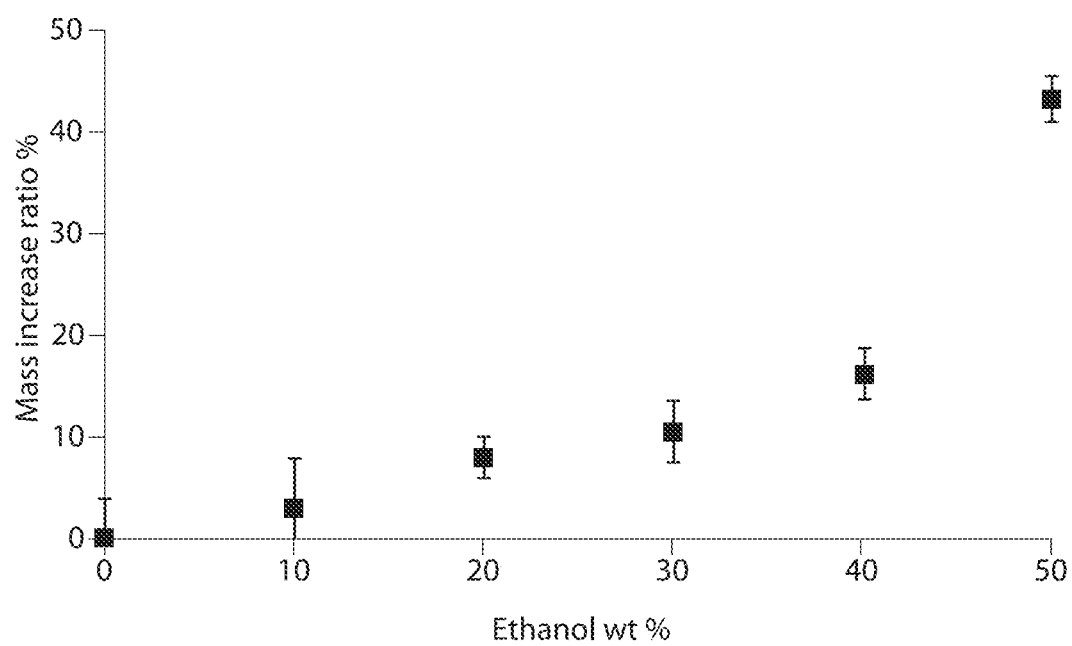
FIG. 9 is a plot of swelling of a polymer in ethanol (pH=2) solution for 24 hours, according to one set of embodiments.

To measure swelling, pre-weighted EEs cubes (~1 cm³) were submerged in either 40 mL SGF blending with certain ratio of vegetable oil (10%) or ethanol (10-50%) in a 50 mL VWR centrifuge tube. 3 replicates for each solvent condition were incubated at 37° C. on a shaker plate at 250 rpm. After 24 hours, samples were weighted and compared with initial weights. For SGF with 10% vegetable oil, EE didn't gain detectable weight. For SGF with ethanol, swelling data is shown in FIG. 9.

Example 3—Fabrication and In Vitro Testing of Gastric Retentive Structures

As a step towards the goal of using EEs as key building blocks in gastric-residence structures, EE and polycaprolactone (PCL) were integrated into a prototype gastric-residence structure. EE with PA6ACA/L100-55 1:2 weight ratio was selected for the fabrication and testing of gastric structures in the rest of this study due to its relatively high tensile strength. For the structural component of the gastric structures, PCL was chosen, which is widely used as a biomaterial for implants and as a drug carrier due to its proven biocompatibility, excellent mechanical properties and ease in manufacturing. Generally, a 3D printer was used to generate positive molds for the generation of negative polydimethylsiloxane (PDMS) molds, then pieces of EE were placed into the molds and melted PCL at 70° C. to interface PCL with the EE for the formation of the integrated EE-PCL structure.

An Objet 3D printer using DurusWhite RGD430 build material and Support Fullcure 705 as support material was used to generate shapes as positive models. Negative molds were created by casting polydimethylsiloxane (PDMS) (SYLGARD® 184 SILICONE ELASTOMER KIT, Dow Corning) around positive models. EE (PA6ACA/L100-55 1:2 ratio) was cut into cubes or cuboids to fit into the PDMS molds and dried by vacuum. Beads of PCL (Sigma, Mn 80 k) were placed between EE pieces in the PDMS molds and melted at 70° C. for 12 hours before cooling to room temperature. Resulting structures bearing EE and PCL were submerged in SGF for 2 days to completely hydrate EE before structures were removed from the molds.

Figure 10:
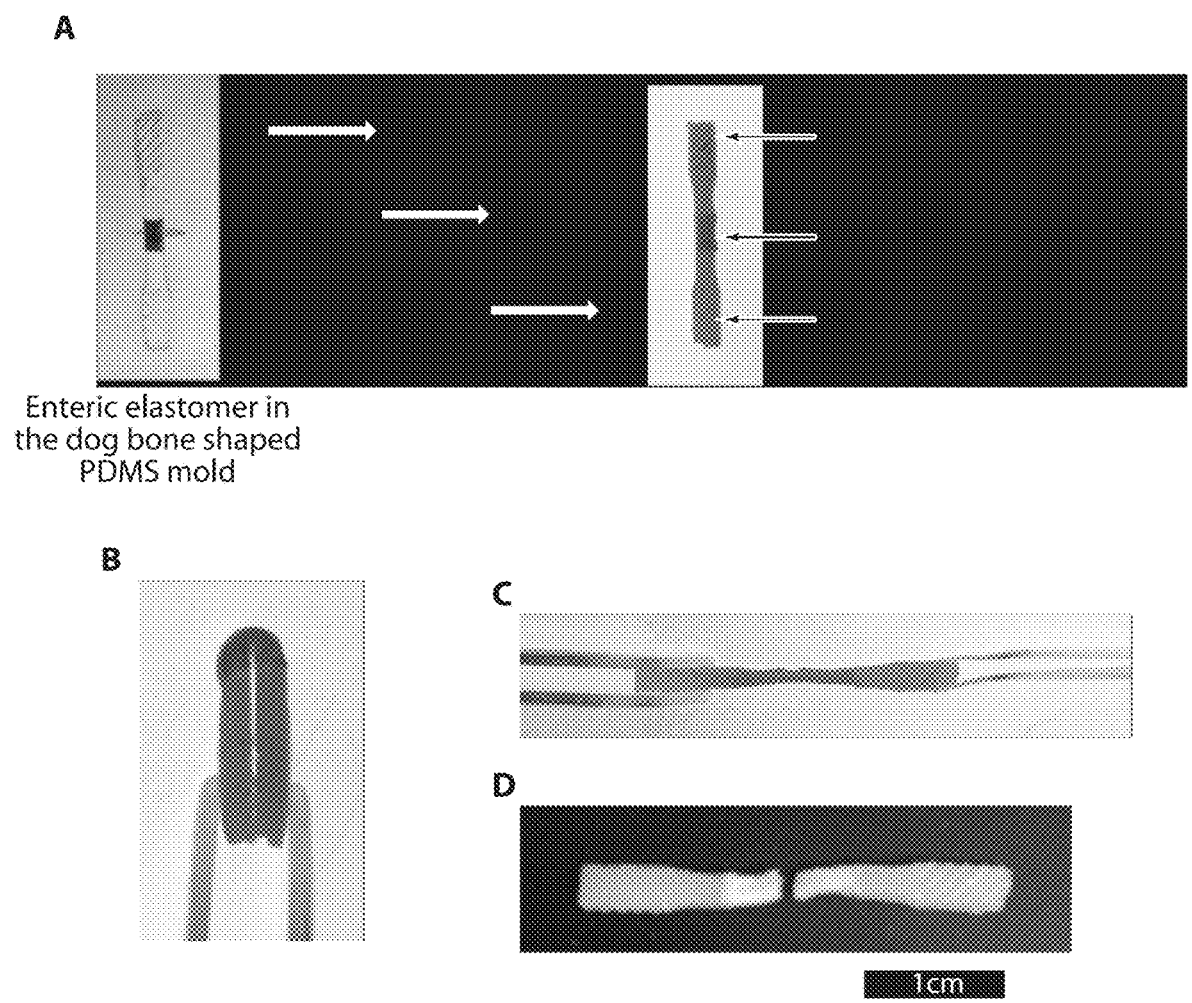
FIG. 10 is a series of photographs illustrating the bending of a polymer composite without breaking, according to one set of embodiments.

To assess the strength and integrity of the joint interface between EE and PCL, EE was placed in the center of a dog-bone shaped structure with PCL on both sides and deformed the dog-bone by 180° as well as linear extension until fracture. As shown in FIG. 10, the EE had a low enough Young's modulus to tolerate 180° bending without breaking. During fracture testing, the EE-to-PCL interfaces were intact, suggesting the stability of the interface and the feasibility of using PCL as a co-building block with EE for the fabrication of gastric resident structures.

Figure 3A:
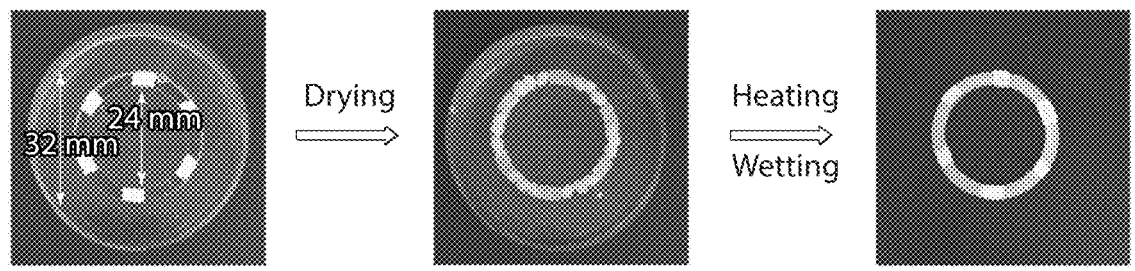
FIG. 3A is a series of photographs for the manufacture of a structure comprising polycaprolactone and polymer composites, according to one set of embodiments.
Figure 3B:
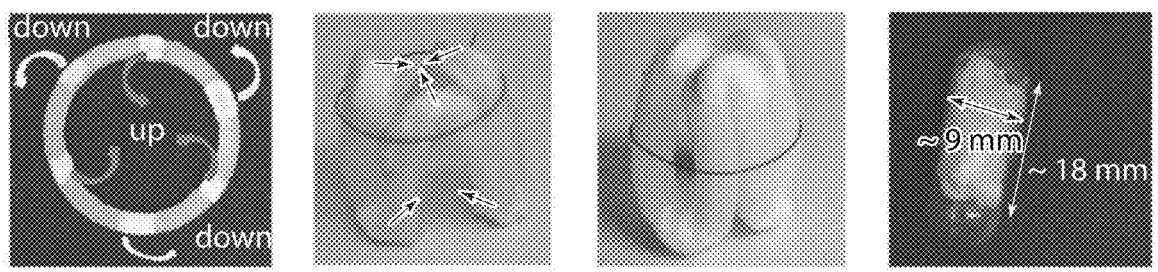
FIG. 3B is a series of photographs illustrating the manufacture of a structure comprising a polymer composite, according to one set of embodiments.
Figure 3C:
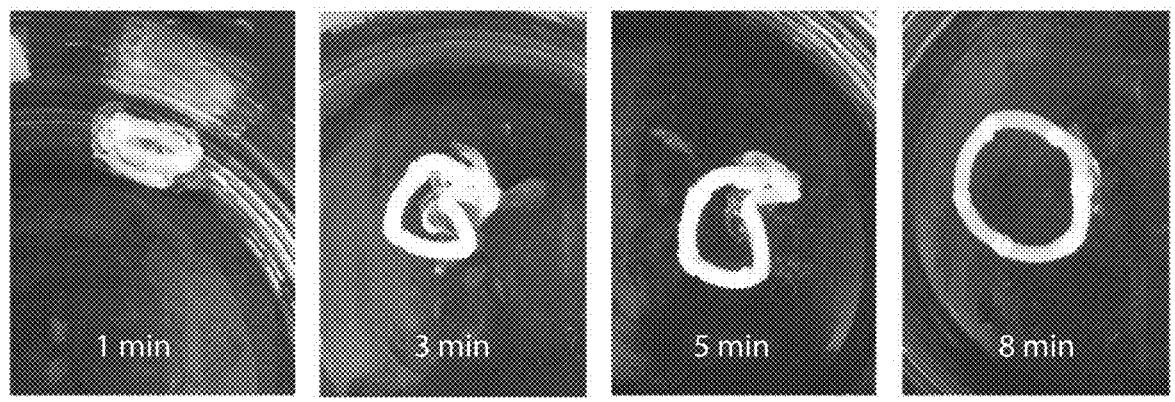
FIG. 3C is a series of photographs of the recovery of a structure comprising a polymer composite, according to one set of embodiments.
Figure 3D:
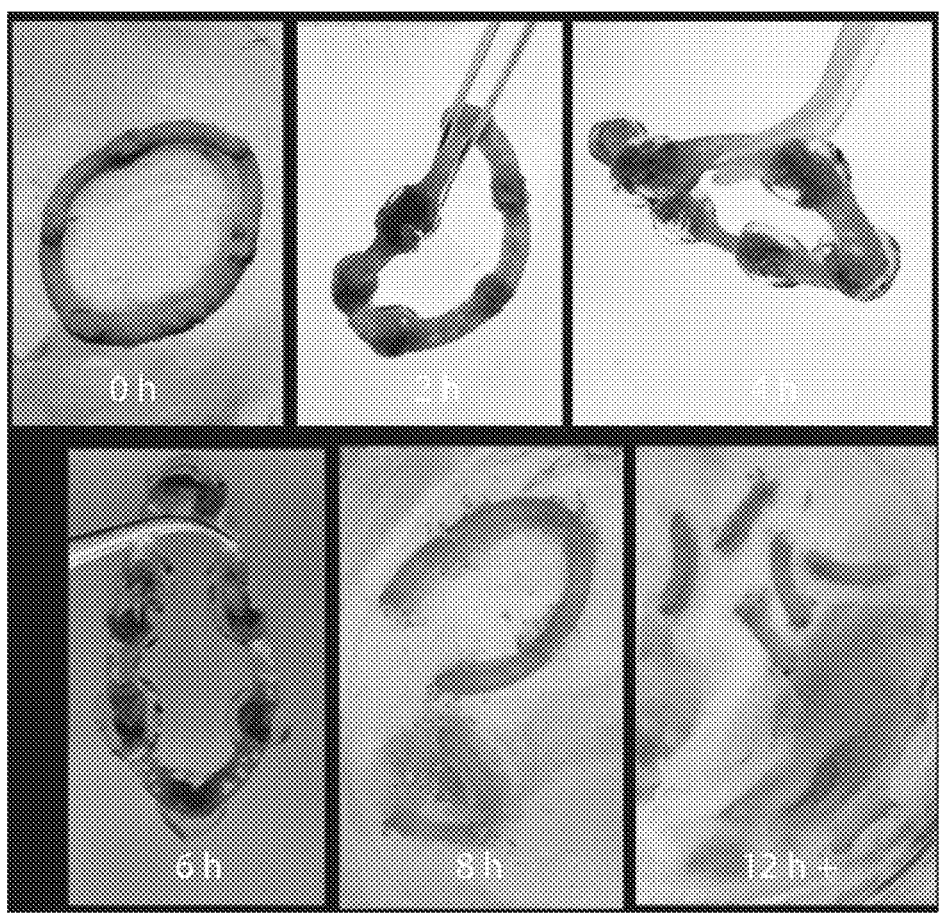
FIG. 3D is a series of photographs of the dissolution of a structure comprising a polymer composite, according to one set of embodiments.

To demonstrate the utility of elastic and enteric functions of EE in gastric structures, a ring composed of PCL arcs with intervening EE linkers was fabricated and tested (FIGS. 3A-3D). The maximal diameter of a structure was selected such that gastric retention occurred by preventing passage through the pylorus. Considering that the aperture diameter of the resting human pylorus is 12.8±7.0 mm, a gastric retentive structure in a ring-shaped PDMS mold with outer diameter of 32 mm, inner diameter of 28 mm, width of 2 mm, and depth of 2 mm, was prepared. EE was cut into cuboid sections with the dimensions 6 mm×4 mm×2 mm, fitted in the molds and then dried by vacuum. This was followed by PCL placement and melting (FIG. 3A). As shown in FIG. 3B, the resulting ring-shaped structure could be encapsulated by bending the elastic components up to 180 degrees to fit into a standard 000 gelatin capsule. To simulate deployment and retention in the stomach environment, the encapsulated circle-shaped structure was placed in SGF at 37° C. The deployed structure escaped from the capsule and recovered its original shape within 8 min (FIG. 3C). The medium was changed to SIF and the EE linkers slowly swelled and dissolved. As a result, the ring-shaped structure gradually disassembled within 12 hours (FIG. 3D). The elastic property of the EE enabled the encapsulation and restoration of the ring-shaped structure following release from the capsule, while the enteric property allowed the dissociation of the structure in SIF.

In Vivo Evaluation of Gastric-Resident Structures in a Large Animal Model

Having established in vitro the elastic and enteric properties imparted by the incorporation of the EE into prototypic structures, the in vivo application of gastric-retentive structures formed with EE was tested using a Yorkshire pig animal model. Yorkshire pigs weighing 45-55 kg generally have gastric and intestinal anatomy and dimensions similar to humans and have been previously used in evaluation of other gastrointestinal structures.

Six separate female Yorkshire pigs weighing approximately 45-55 kg were used for in vivo evaluation. Prior to the procedures the animals were fasted overnight. On the day of the procedure, the morning feed was held and the animals were sedated with Telazol (tiletamine/zolazepam) 5 mg/kg, xylazine 2 mg/kg, and atropine 0.04 mg/kg. To ensure gastric placement of the structures the structures were placed in the stomach with the use of an esophageal overtube (US Endoscopy, Mentor, Ohio) which was placed endoscopically in the esophagus. Radiographs were performed every 48-72 hours to monitor the integrity and transit of the structures as well as any radiographic evidence of bowel obstruction or perforation. Furthermore all animals were monitored clinically at least twice a day for any evidence of obstruction including poor feeding, poor defecation, abdominal distension and vomiting. Where radio-opaque fiducials were omitted from prototype structures visualization was performed endoscopically.

Figure 4A:
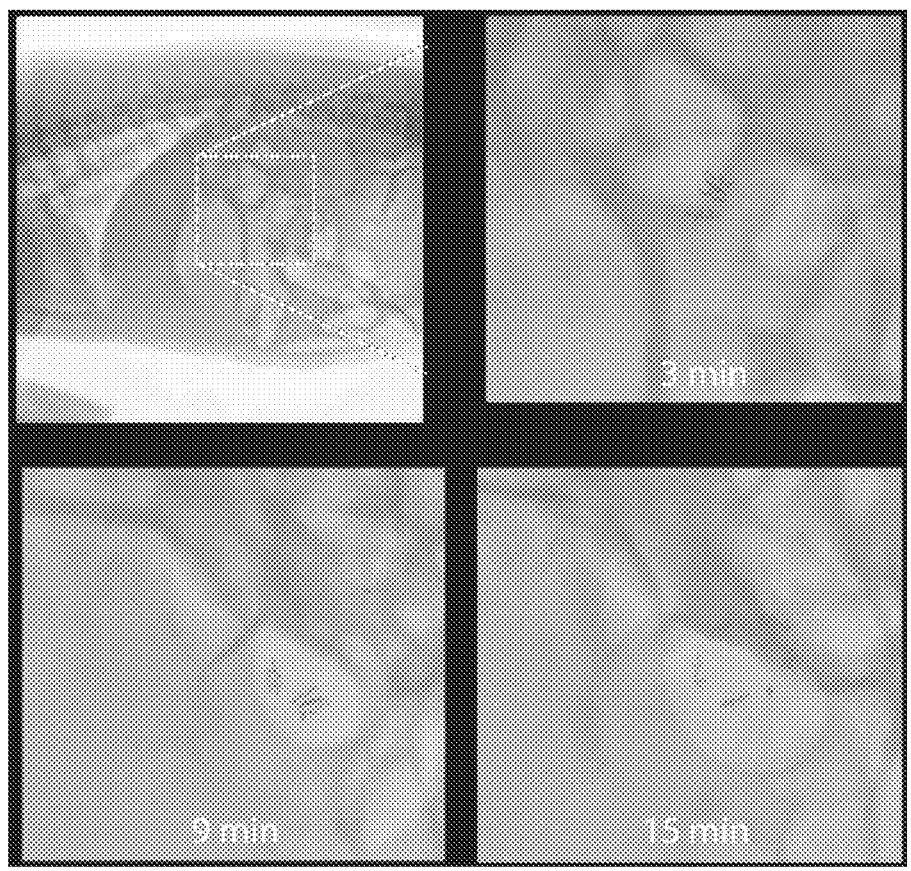
FIG. 4A is a series of in vivo photographs of recovery of a ring shape after delivery of an encapsulated ring-shaped structure through the esophagus and dissolution of the gelatin capsule in stomach, comprising a polymer composite, according to one set of embodiments.
Figure 4B:
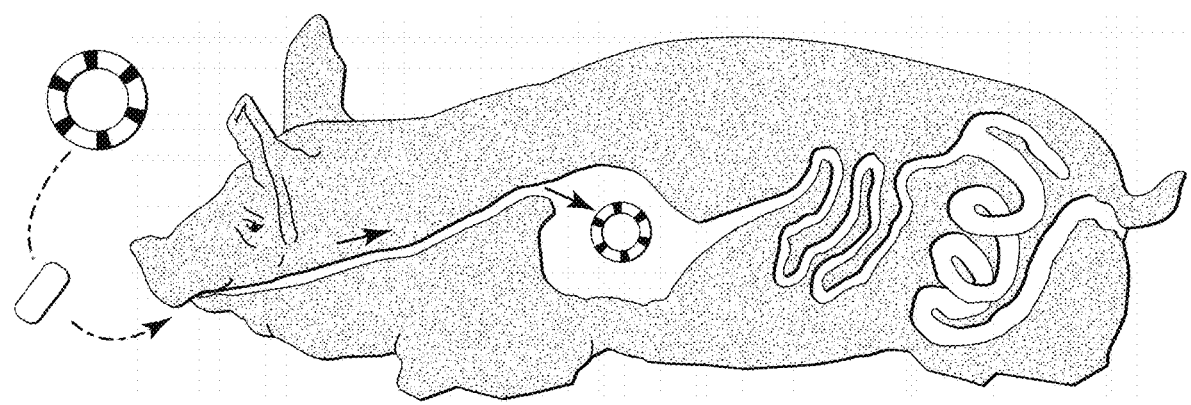
FIGS. 4B-4C are schematics of the (B) delivery and (C) passage upon dissociation of a structure comprising a polymer composite, according to one set of embodiments.
Figure 4C:
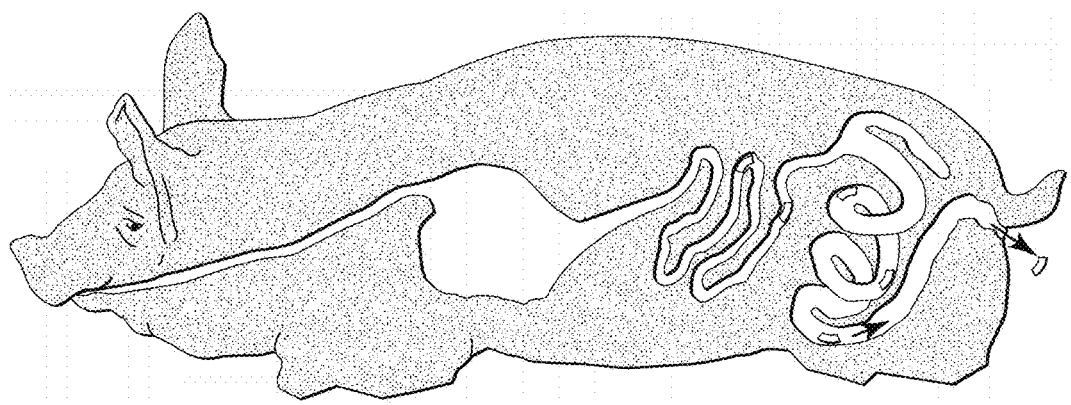
Figure 4D:
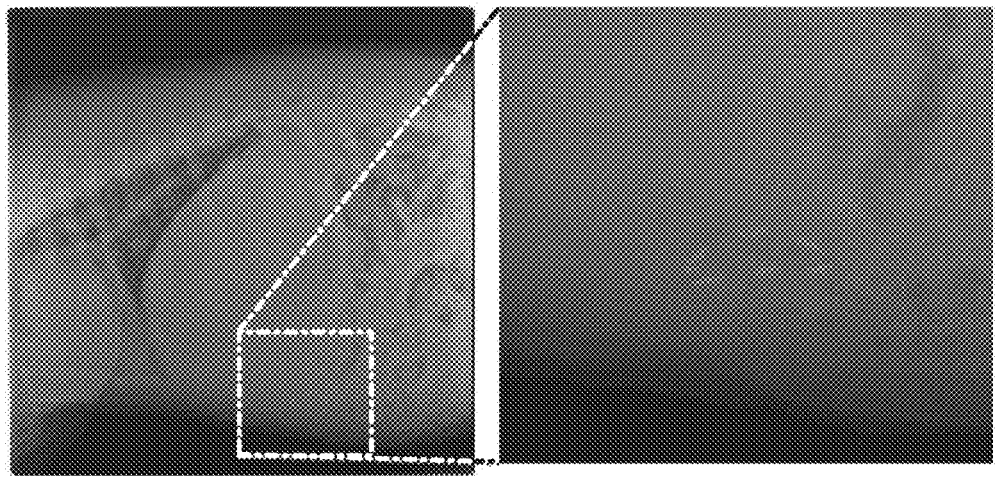
FIG. 4D is an X-ray image of a ring-shaped structure residing in the gastric cavity of a Yorkshire pig, according to one set of embodiments.
Figure 4E:
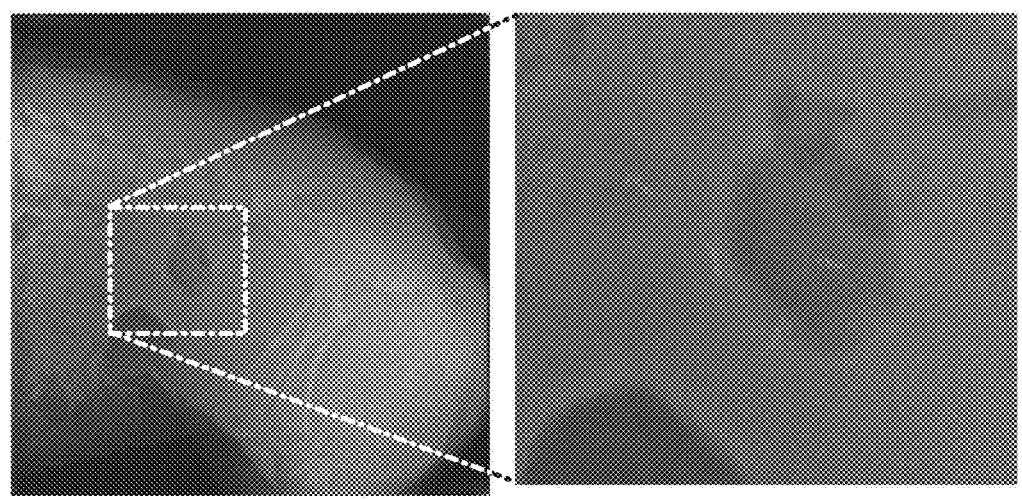
FIG. 4E is an X-ray image of four PCL arcs passing through the intestine after dissolution of the polymer composite, according to one set of embodiments.
Figure 11:
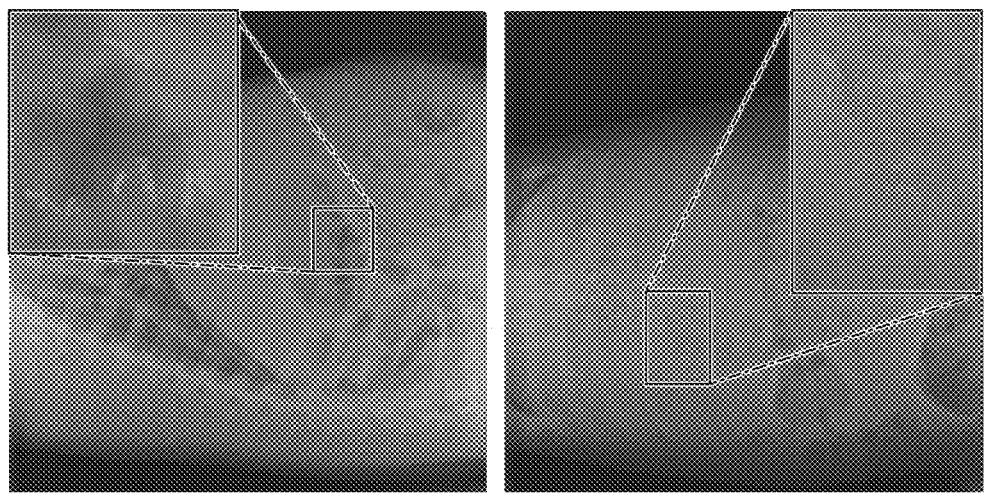
FIG. 11 show X-ray images of structures comprising polymer composites, according to one set of embodiments.

Ring-shaped structures as depicted in FIGS. 3A-3D were formed and encapsulated in 000 gelatin capsules with the addition of 1 mm stainless steel balls within the PCL arms for radiographic monitoring. Under moderate sedation, the capsule was introduced through the esophagus under endoscopic visualization. The encapsulated ring-shaped structure deployed and restored its baseline shape in the stomach within 15 min (FIG. 4A). Four individual experiments on four different pigs were performed demonstrating gastric retention of the structure for 2-5 days (FIG. 4B and FIG. 4D). No intact structures were visualized outside of the stomach suggesting structure breakage first occurred in the stomach. Loss of the intact structure was visualized radiographically where the partial dissolution and/or rupture of one or two EE linkers was noted resulting in linearization of the closed structure enabling easier passage out of the stomach (FIG. 11). Upon passage out of the stomach the dissolvable EEs disintegrated resulting in the small fragments enabling safe passage of the rigid segment without evidence of intestinal obstruction (FIG. 4C and FIG. 4E). Through all the experiments the animals were observed to have normal eating and stooling patterns and did not display any signs of gastrointestinal obstruction either clinically or radiographically. Radiographic visualization for the experiments above was enabled by the inclusion of radio-opaque beads in the PCL segments of the structures.

Figure 12:
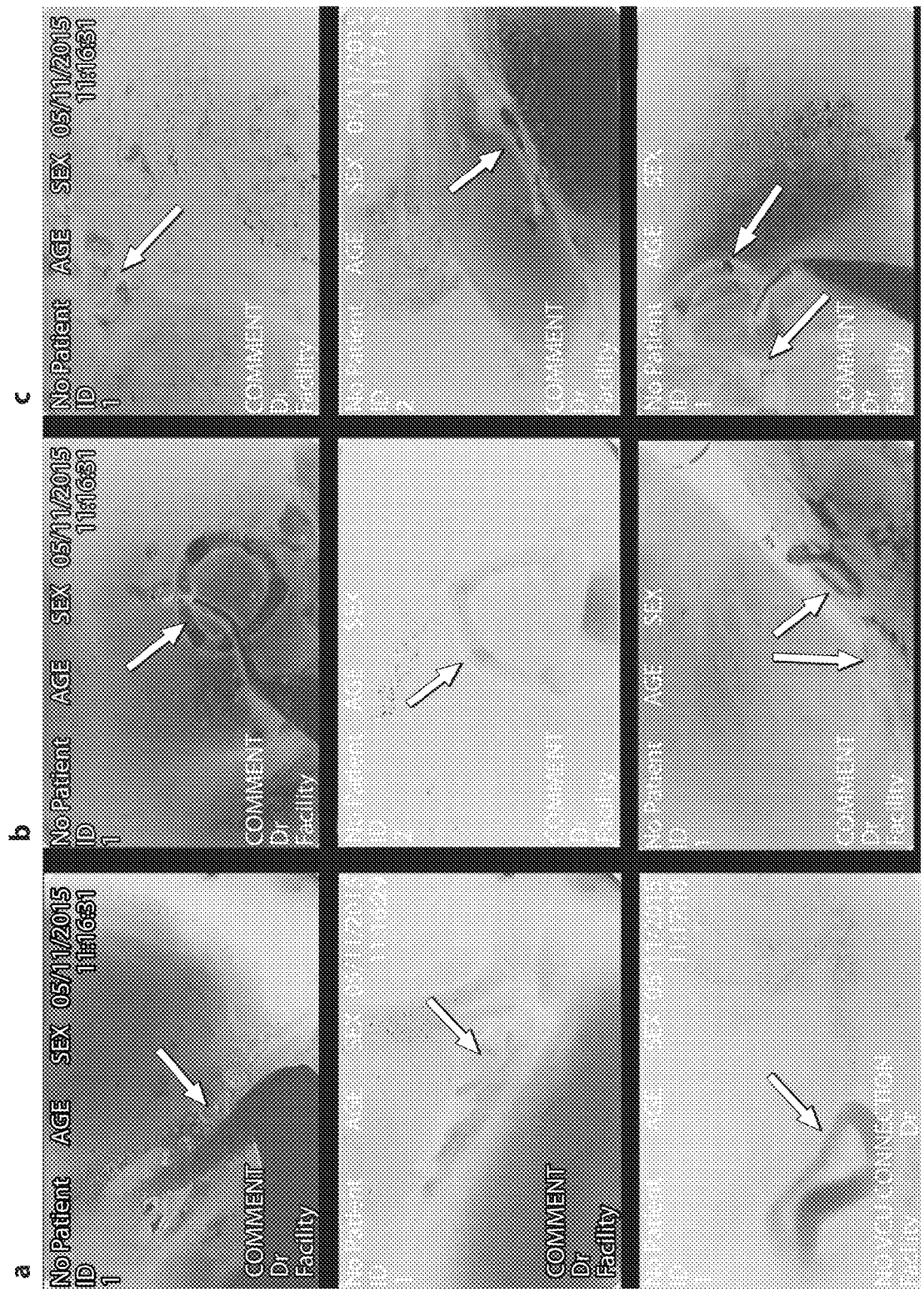
FIG. 12 is a series of endoscopic photographs of in vivo structures after 30 days, 2 days, and 4 days of gastric residence, according to one set of embodiments.

To evaluate the possibility that the stainless steel beads in the PCL arms contributed to gastric retention, four encapsulated ring-shaped structures without iron beads were deployed into two pigs (two capsules per each animal). Endoscopic imaging was used to evaluate these in the gastric cavity at the time points of 0.5 hour, 2 days, 4 days and 7 days post deployment. All four rings were identified and were intact in the stomachs of the 2 animals after 2 days and 4 days, while only one ring was identified after 7 days (FIG. 12). Gastric retention did not appear to be significant affected by the elimination of the stainless steel beads which represented ~20% of the total mass of the structure.

The elastic function of the EE generally enabled the circle-shaped structure to be folded into the standard 000 capsule for comfortable oral delivery and also enabled shape recovery for prolonged gastric retention, after dissolution of the capsule. The enteric function generally permitted the dissociation of the structure into small pieces for safe passage through the lower gastrointestinal tract. This prototype structure achieved extended gastric retention for 2-7 days, when compared to the maximum of 1-2 days of gastric retention achieved by other reported gastric retentive structures delivered by capsules.

Figure 5A:
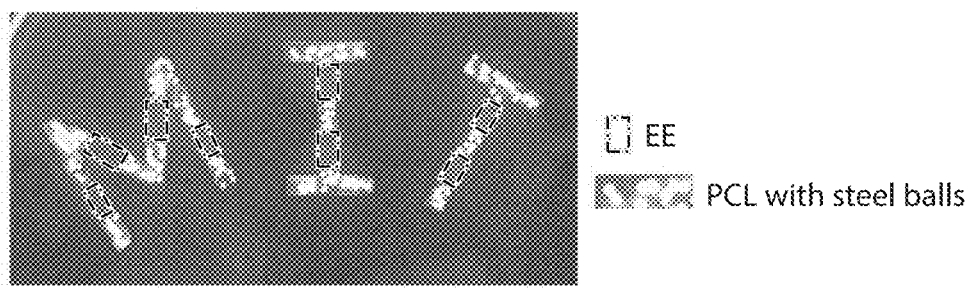
FIGS. 5A-5J are a series of x-ray and endoscopic images showing gastric residence of various shaped structures comprising a polymer composite, according to one set of embodiments.
Figure 5B:
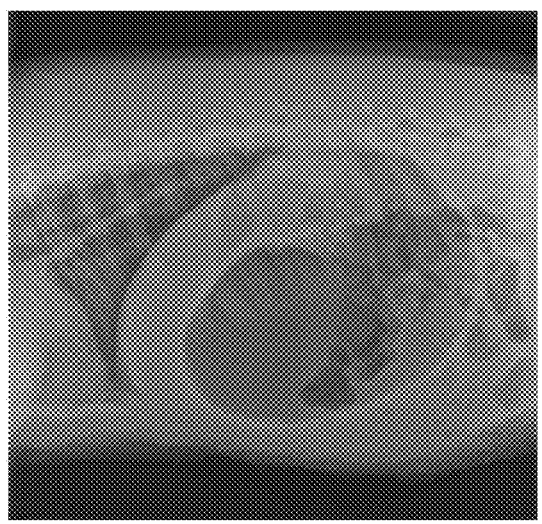
Figure 5C:
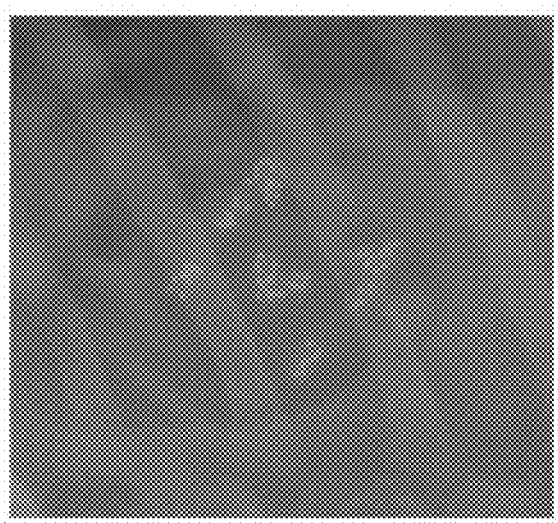
Figure 5D:
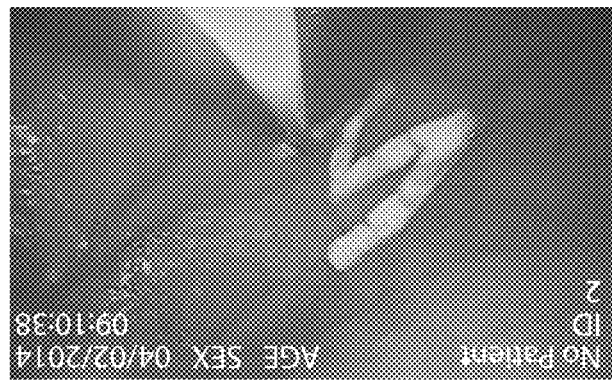
Figure 5E:
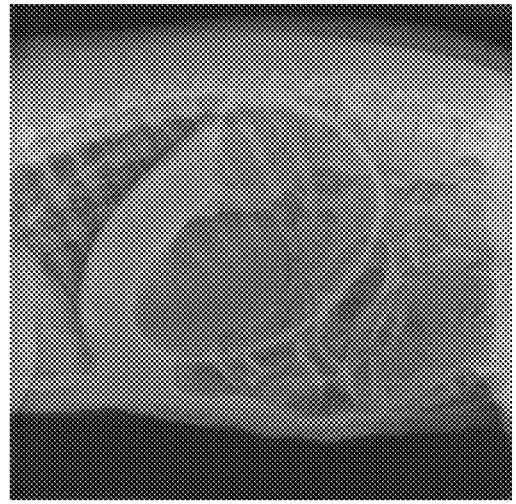
Figure 5F:
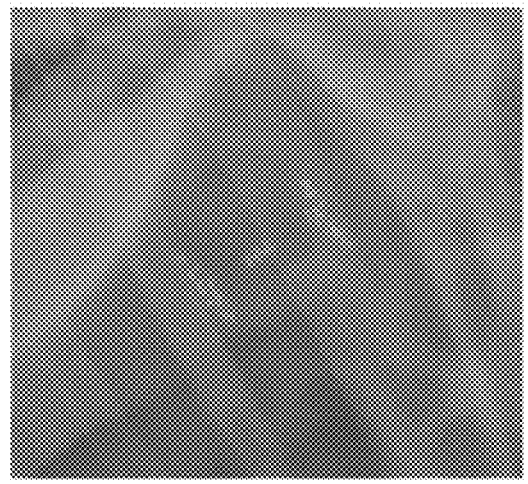
Figure 5G:
Figure 5H:
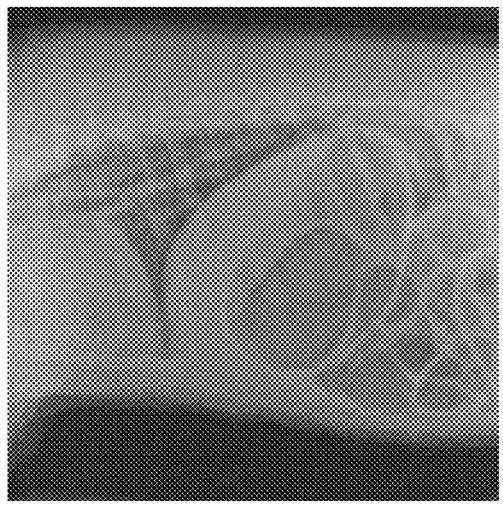
Figure 5I:
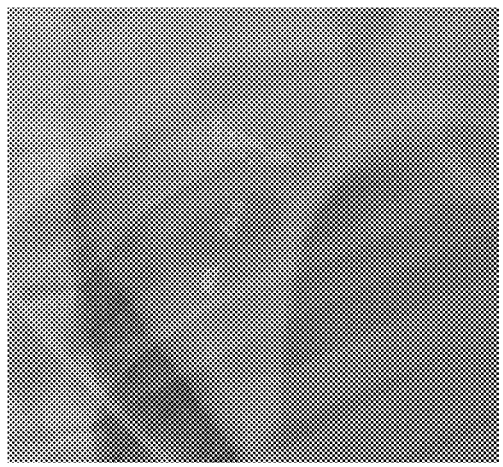
Figure 5J:
Figure 6A:
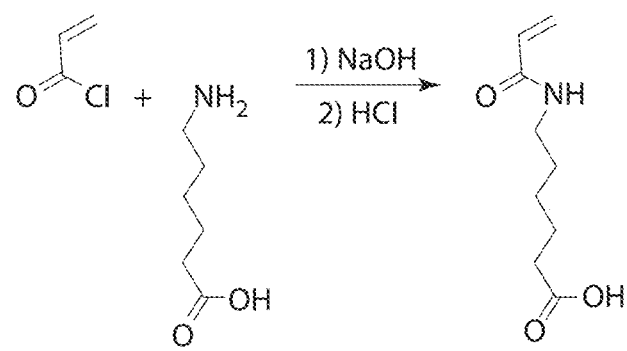
FIGS. 6A-6D are schematics of various polymers used in the formation of a polymer composite, according to some embodiments.
Figure 6B:
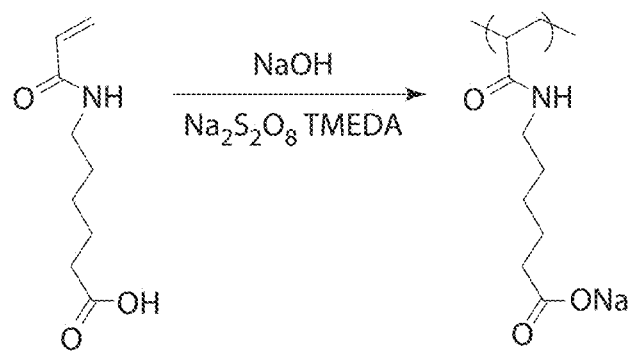
Figure 6C:
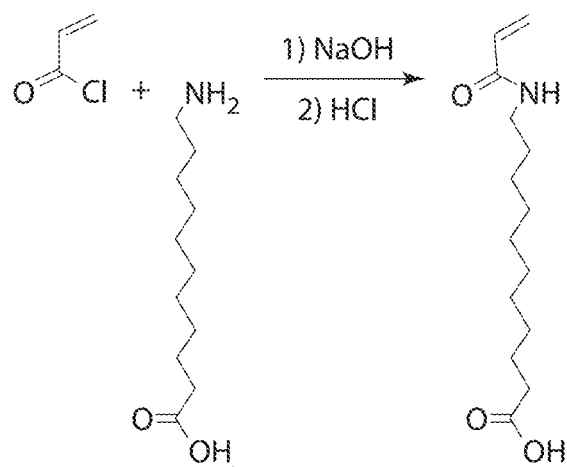
Figure 6D:
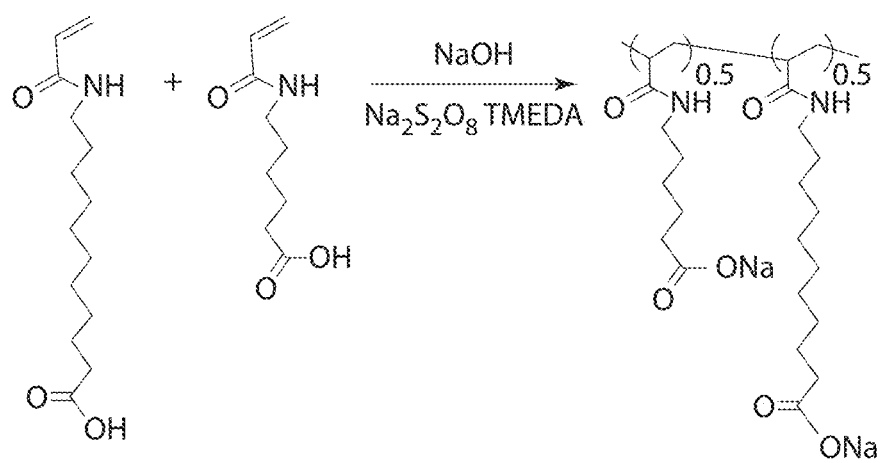
Figure 13:
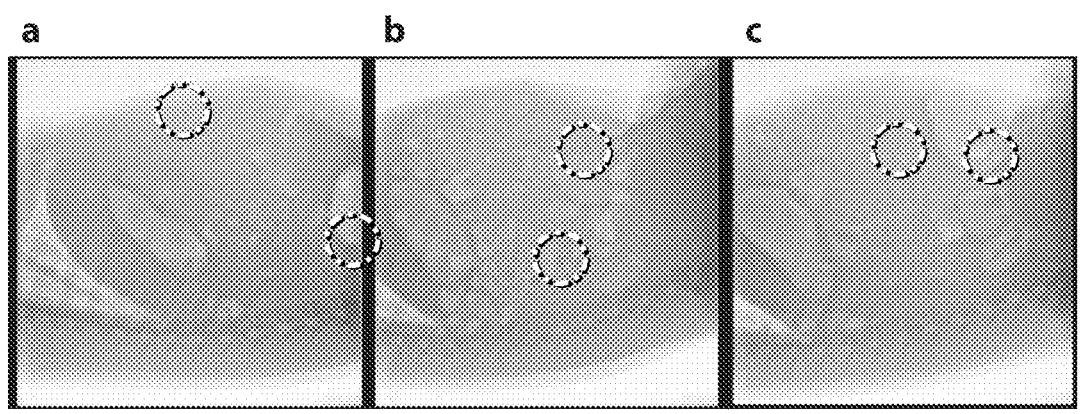
FIG. 13 is a series of X-ray images of various shape structures comprising a polymer composite passing through the intestine after dissolution of the polymer composite, according to one set of embodiments.

Beyond the self-deployable gastric-retentive structure delivered by capsules, exemplary gastric-resident structures for the endoscopic delivery and placement we explored, including large structures composed similarly of PCL rigid segments linked together with EE and that formed the letters "M.I.T.". Those exemplary gastric-resident structures were constructed with EE and PCL embedded with iron balls by using M-, I-, and T-shaped PMDS molds. These shapes could be folded and delivered through the esophagus with endoscopic assistance. Radiographic images show elastic restoration of the M, I, and T-letter shapes in three pig stomachs (FIGS. 5B-5C, 5E-5F, and 5H-5I) right after delivery. Endoscopic images also confirmed gastric retention of all three letters, and found no obstruction caused by those structures (FIGS. 5D, 5G, and 5J). All three M, I, and T-shaped structures were retained in the gastric cavity for 2-5 days before the fragmentation (FIG. 13).

Example 4—Synthesis

Materials.

6-Aminocaproic acid, 11-aminoundecanoic acid, NaOH, hydrochloric acid (ACS reagent, 37%), NaCl, tetramethylethylenediamine, ammonium persulfate, polycaprolactone (PCL, average Mn 80,000) and $KH_2PO_4$ were used as received from Sigma-Aldrich Company (St. Louis, Mo.). Acryloyl chloride was purchased from Sigma and vacuum distilled before using. Nanopure water (18 MΩ·cm) was acquired by means of a Milli-Q water filtration system, Millipore Corp. (St. Charles, Mo.). 1 L of simulated gastric fluid (SGF, pH~1.2) was made by dissolving 2 g NaCl and 8.3 mL concentrated HCl in water and adjusting to 1000 mL with water. 1 L of simulated intestinal fluid (SGF, pH~6.8) was made by dissolving 6.8 g $KH_2PO_4$ and 0.896 g NaOH in water and adjusting to 1000 mL with water.

Synthesis of PA6ACA Sodium Salt.

To a nitrogen bubbled solution containing 10 g (54.1 mmol) A6ACA, 2.16 g (54.1 mmol) NaOH, and 6.3 mg (0.0541 mmol) tetramethylethylenediamine (TMEDA) dissolved in 400 mL nanopure water at 40° C. was added a solution of 62 mg (0.270 mmol) ammonium persulfate in 10 mL nanopure water. The reaction mixture was allowed to stir for 12 h for the polymerization. The polymer solution was transferred to dialysis tubes (MWCO 3500 Da) for dialysis for three days and lyophilized, obtaining a white solid powder with an average yield of 95%.

Synthesis of P(A6ACA$_{0.5}$-co-A11AUA$_{0.5}$) Sodium Salt.

To a nitrogen bubbled solution containing 10 g (39.2 mmol) A11AUA, 7.25 g (39.2 mmol) A6ACA, 3.14 g (78.4 mmol) NaOH, and 9.1 mg (0.0784 mmol) tetramethylethylenediamine (TMEDA) in 700 mL nanopure water at 40° C. was added a solution of 89 mg (0.392 mmol) ammonium persulfate in 10 mL nanopure water. The reaction mixture was allowed to stir for 12 h for the polymerization. The polymer solution was transferred to dialysis tubes (MWCO 3500 Da) for dialysis for three days and lyophilized, obtaining a white solid powder with an average yield of 87%. 50:50 composition ratio of P(A6ACA$_{0.5}$-co-A11AUA$_{0.5}$) was the feeding ratio of the radical polymerization.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:
1. A polymer composite, comprising:
a first polymer comprising a structure as in Formula (I):

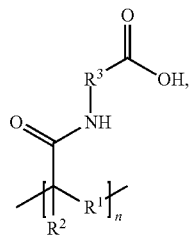

(I)

or a pharmaceutically acceptable salt thereof, wherein:
each $R^1$ is the same or different and is selected from the group consisting of optionally substituted alkylene, optionally substituted heteroalkylene, optionally substituted arylene, and optionally substituted heteroarylene;
each $R^2$ is the same or different and is selected from the group consisting of hydrogen, optionally substituted alkyl, and optionally substituted heteroalkyl;
each $R^3$ is the same or different and is selected from the group consisting of optionally substituted alkylene and optionally substituted heteroalkylene;
n is an integer between 25 and 250,000; and
a second polymer comprising a structure as in Formula (II) hydrogen bonded to the first polymer:

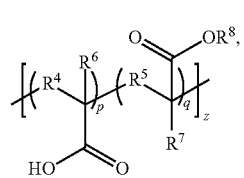

(II)

or a pharmaceutically acceptable salt thereof, wherein:
each $R^4$ is the same or different and is selected from the group consisting of optionally substituted alkylene and optionally substituted heteroalkylene;
each $R^5$ is the same or different and is selected from the group consisting of optionally substituted alkylene and optionally substituted heteroalkylene;
each $R^6$ is the same or different and is selected from the group consisting of hydrogen, optionally substituted alkyl, and optionally substituted heteroalkyl;
each $R^7$ is the same or different and is selected from the group consisting of hydrogen, optionally substituted alkyl, and optionally substituted heteroalkyl;
each $R^8$ is the same or different and is optionally substituted alkyl;
p is an integer between 1 and 10;
q is an integer between 1 and 10; and
z is an integer between 1 and 150,000, provided that $(p+q)*z$ is greater than or equal to 20.

2. A polymer composite as in claim 1, wherein the polymer composite is elastic.

3. A polymer composite as in claim 1, wherein the polymer composite may be configured for undergoing at least about 45 degrees, at least about 60 degrees, at least about 90 degrees, at least about 120 degrees, at least about 150 degrees, or at least about 180 degrees of mechanical bending deformation without breaking.

4. A polymer composite as in claim 1, wherein the polymer composite has a strength of recoil sufficient to substantially return the polymer composite to its pre-deformed shape in less than about 30 minutes, in less than about 10 minutes, in less than about 5 minutes, or in less than about 1 minute after release of the mechanical deformation.

5. A polymer composite as in claim 1, wherein the polymer composite exhibits reversible elongation when stretched from 50% to 1500% of its initial length.

6. A polymer composite as in claim 1, where the polymer composite has an elastic modulus ranging between about 0.1 MPa and about 100 MPa.

7. A polymer composite as in claim 1, wherein the polymer composite is enteric.

8. A polymer composite as in claim 1, wherein the polymer composite is stable at a pH less than about 5 and dissolves at a pH greater than about 5.5.

9. A polymer composite as in claim 1, wherein:
each $R^1$ is the same or different and is selected from the group consisting of optionally substituted alkylene and optionally substituted heteroalkylene;
each $R^2$ is the same or different and is selected from the group consisting of hydrogen and optionally substituted alkyl;
each $R^3$ is the same or different and is selected from the group consisting of optionally substituted alkylene and optionally substituted heteroalkylene; and
n is an integer between 25 and 250,000.

10. A polymer composite as in claim 1, wherein:
each $R^1$ is the same or different and is —$[C(R'_2)]_g$—;
each $R^2$ is the same or different and is selected from the group consisting of hydrogen and optionally substituted alkyl;
each $R^3$ is the same or different and is selected from the group consisting of optionally substituted $C_{2-10}$ alkylene and optionally substituted hetero $C_{2-8}$ alkylene;
each R' is the same or different and is selected from the group consisting of hydrogen and optionally substituted alkyl;
g is 1, 2, 3, 4, or 5; and
n is an integer between 25 and 250,000.

11. A polymer composite as in claim 1, wherein:
each $R^1$ is the same or different and is —$[C(R'_2)]_g$—;
each $R^2$ is the same or different and is selected from the group consisting of hydrogen and optionally substituted alkyl;
each $R^3$ is the same or different and is selected from the group consisting of optionally substituted $C_{4-8}$ alkylene and —$(CH_2CH_2O)_m$—;
each R' is the same or different and is selected from the group consisting of hydrogen and optionally substituted alkyl;
g is 1, 2, 3, 4, or 5;
m is 1, 2, or 3; and
n is an integer between 25 and 250,000.

12. A polymer composite as in claim 1, wherein the first polymer comprises a structure as in:

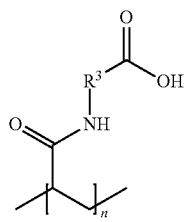

or a pharmaceutically acceptable salt thereof, wherein:
$R^3$ is the same or different and is selected from the group consisting of optionally substituted $C_{4-8}$ alkylene and —$(CH_2CH_2O)_m$—;
m is 1, 2, or 3; and
n is an integer between 25 and 250,000.

13. A polymer composite as in claim 1, wherein the first polymer comprises a structure as in:

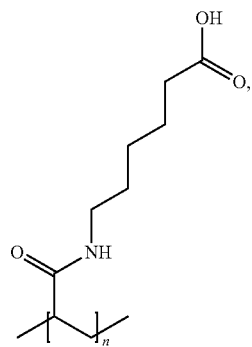

or a pharmaceutically acceptable salt thereof, wherein n is an integer between 25 and 250,000.

14. A polymer composite as in claim 1, wherein the first polymer is selected from the group consisting of a polymer of an acryloylaminoalkylene acid monomer, or salts thereof.

15. A polymer composite as in claim 14 wherein the acryloylaminoalkylene acid monomer is selected from the group consisting of acryloyl-5-aminopentanoic acid, acryloyl-6-aminocaproic acid, acryloyl-7-aminoheptanoic acid, acryloyl-8-aminooctanoic acid, acryloyl-9-aminononaoic acid, acryloyl-10-aminodecanoic acid, acryloyl-11-aminoundecanoic acid, acryloyl-12-aminododecanoic acid, methacryloyl-5-aminopentanoic acid, methacryloyl-6-aminocaproic acid, methacryloyl-7-aminoheptanoic acid, methacryloyl-8-aminooctanoic acid, methacryloyl-9-aminononanoic acid, methacryloyl-10-aminodecanoic acid, methacryloyl-11-aminoundecanoic acid, methacryloyl-12-aminododecanoic acid, salts thereof, and combinations thereof.

16. A polymer composite as in claim 1, wherein the first polymer is a homopolymer of acryloyl-6-aminocaproic acid or salts thereof.

17. A polymer composite as in claim 1, wherein:
each $R^4$ is the same or different and is optionally substituted alkylene;
each $R^5$ is the same or different and is optionally substituted alkylene;
each $R^6$ is the same or different and is selected from the group consisting of hydrogen and optionally substituted alkyl;
each $R^7$ is the same or different and is selected from the group consisting of hydrogen and optionally substituted alkyl;
each $R^8$ is the same or different and is optionally substituted alkyl;
p is an integer between 1 and 10;
q is an integer between 1 and 10; and
z is an integer between 1 and 150,000, provided that (p+q)*z is greater than or equal to 20.

18. A polymer composite as in claim 1, wherein:
each $R^4$ the same or different and is —$[C(R''_2)]_e$—;
each $R^5$ is the same or different and is —$[C(R''_2)]_e$—;
each $R^6$ is the same or different and is selected from the group consisting of hydrogen and optionally substituted alkyl;
each $R^7$ is the same or different and is selected from the group consisting of hydrogen and optionally substituted alkyl;
each $R^8$ is the same or different and is optionally substituted alkyl;
each R" is the same or different and is selected from the group consisting of hydrogen and optionally substituted alkyl;

p is an integer between 1 and 10;
q is an integer between 1 and 10;
e is 1, 2, 3, 4, or 5; and
z is an integer between 1 and 150,000, provided that (p+q)*z is greater than or equal to 20.

19. A polymer composite as in claim 1, wherein the first polymer comprises a structure as in:

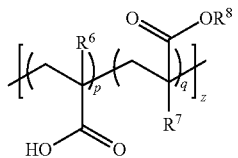

or a pharmaceutically acceptable salt thereof, wherein:
each $R^6$ and $R^7$ is the same or different and is selected from the group consisting of hydrogen and optionally substituted alkyl;
each $R^8$ is the same or different and is optionally substituted alkyl;
p is an integer between 1 and 10;
q is an integer between 1 and 10; and
z is an integer between 1 and 150,000, provided that (p+q)*z is greater than or equal to 20.

20. A polymer composite as in claim 1, wherein the first polymer comprises a structure as in:

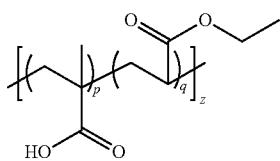

or a pharmaceutically acceptable salt thereof, wherein:
p is an integer between 1 and 10;
q is an integer between 1 and 10; and
z is an integer between 1 and 150,000, provided that (p+q)*z is greater than or equal to 20.

21. A polymer composite as in claim 1, wherein the ratio of the first polymer to the second polymer is between about 6:1 to about 1:6.

22. A polymer composite as in claim 1, wherein the first polymer is poly(acryloyl-6-aminocaproic acid) and the second polymer is poly(methacrylic acid-co-ethyl acrylate).

23. A polymer composite as in claim 22, wherein the poly(methacrylic acid-co-ethyl acrylate) has a molar ratio of methacrylic acid monomer units to ethylacrylate monomer units of about 1:1.

24. A polymer composite as in claim 1, wherein the polymer composite has a water content no greater than about 40 wt %.

25. A polymer composite as in claim 1, wherein the polymer composite comprises an active substance.

26. A polymer composite as claim 25, wherein the active substance comprises at least one of a statin, an anti-malarial agent, a hormone, levothyroxine, ivermectin, antiretroviral agents, antihelminth agents, antipsychotics, antidepressants, and caffeine.

27. A gastric residence structure comprising a polymer composite as in claim 1.

28. An enteric polymer, wherein the enteric polymer comprises a polymer composite as in claim 1.

* * * * *